US006100027A

United States Patent [19]

Yang et al.

[11] Patent Number: 6,100,027

[45] Date of Patent: *Aug. 8, 2000

[54] NUCLEIC ACID PROBES AND AMPLIFICATION OLIGONUCLEOTIDES FOR NEISSERIA SPECIES

[75] Inventors: Yeasing Yang, San Diego; Gary Bee, Vista; Sherrol McDonough, San Diego, all of Calif.

[73] Assignee: Gen-Probe Incorporated, San Diego, Calif.

[ * ] Notice: This patent is subject to a terminal disclaimer.

[21] Appl. No.: 08/962,369

[22] Filed: Oct. 31, 1997

Related U.S. Application Data

[63] Continuation of application No. 08/484,607, Jun. 7, 1995, Pat. No. 5,747,252.

[51] Int. Cl.[7] .............................. C12Q 1/68; C12P 19/34; C07H 21/02; C07H 21/04

[52] U.S. Cl. ............................ 435/6; 435/91.1; 435/91.2; 435/91.5; 536/23.1; 536/24.3; 536/24.31; 536/24.32; 536/24.33

[58] Field of Search .............................. 435/6, 91.1, 91.2, 435/91.5; 536/23.1, 24.3, 24.31, 24.32, 24.33

[56] References Cited

U.S. PATENT DOCUMENTS

| | | | |
|---|---|---|---|
| 4,851,330 | 7/1989 | Kohne . | |
| 5,030,557 | 7/1991 | Hogan et al. . | |
| 5,047,523 | 9/1991 | Woods et al. . | |
| 5,079,351 | 1/1992 | Sninsky et al. . | |
| 5,173,401 | 12/1992 | Wolff et al. . | |
| 5,185,439 | 2/1993 | Arnold . | |
| 5,216,143 | 6/1993 | Hogan et al. . | |
| 5,217,862 | 6/1993 | Barns et al. . | |
| 5,256,536 | 10/1993 | Miyada et al. . | |
| 5,283,174 | 2/1994 | Arnold . | |
| 5,399,491 | 3/1995 | Kacian et al. . | |
| 5,432,271 | 7/1995 | Barns et al. . | |
| 5,747,252 | 5/1998 | Yang et al. | 435/6 |

FOREIGN PATENT DOCUMENTS

| | | |
|---|---|---|
| 0272009 | 6/1988 | European Pat. Off. . |
| 0309230 | 3/1989 | European Pat. Off. . |
| 0313219 | 4/1989 | European Pat. Off. . |
| 0318245 | 5/1989 | European Pat. Off. . |
| 0337896 | 10/1989 | European Pat. Off. . |
| 0452596 | 10/1991 | European Pat. Off. . |
| 0552931 | 7/1993 | European Pat. Off. . |
| 8803957 | 6/1988 | WIPO . |
| 9014442 | 11/1990 | WIPO . |
| 0404161 | 12/1990 | WIPO . |
| 0439330 | 7/1991 | WIPO . |
| 9204358 | 3/1992 | WIPO . |
| 9207864 | 5/1992 | WIPO . |
| 9303186 | 2/1993 | WIPO . |
| 9324659 | 12/1993 | WIPO . |
| 9403472 | 2/1994 | WIPO . |
| 9606949 | 3/1996 | WIPO . |

OTHER PUBLICATIONS

Adams et al. (editors), "Ch. 2—The Structure of the nucleic acids," *The Biochemistry of the Nucleic Acids, 11th Edition*, Chapman & Hall, New York, pp. 5–39 (1992).

Auriol et al., "Characterization of serogroup A *Neisseria meningitidis* strains by rRNA gene restriction patterns and PCR: correlation with results of serotyping, subtyping and multilocus enzyme electrophoresis," *FEMS Immunology and Medical Microbiology* 10:219–226 (1995).

Barone et al., "In situ activities of bis–dialkylaminophosphines—a new method for synthesizing deoxyoligonucleotides on polymer supports," *Nucleic Acids Research* 12:4051–4061 (1984).

Birkenmeyer and Armstrong, "Preliminary Evaluation of the Ligase Chain Reaction for Specific Detection of *Neisseria gonorrhoeae*," *J. Clin. Microbiol.* 30:3089–3094 (1992).

Enright et al., "Phylogenetic relationships between some members of the genera Neisseria, Acinetobacter, Moraxella and Kingella based on partial 16S ribosomal DNA sequence analysis," *Int. J. Syst. Bacteriol.* 44(3):387–391 (1994).

Greisen et al., "PCR primers and probes for the 16S rRNA gene of most species of pathogenic bacteria, including bacteria found in cerebrospinal fluid," *J. Clin. Microbiol.* 32(2):335–351 (1994).

Griffith, "Amino Acid Sulfoximines: α–Ethylmethionine Sulfoximine," *Methods in Enzymology* 143:287–291 (1987).

Linz et al., "Systematic Studies on Parameters Influencing the Performance of the Polymerase Chain Reaction," *J. Clin. Chem. Clin. Biochem.* 28:5–13 (1990).

McLaughlin et al., "Amplification of rDNA loci to detect and type *Neisseria meningitidis* and other eubacteria," *Molecular and Cellular Probes* 7:7–17 (1993).

Muralidhar and Steinman, "Design and characterization of PCR primers for detection of pathogenic Neisseriae," *Molecular and Cellular Probes* 8:55–61 (1994).

Nelson, "Detection of Acridinium Esters by Chemiluminescence," in *Nonisotopic DNA Probe Techniques*, edited by Kricka, Academic Press, Inc., San Diego, pp. 275–310 (1992).

(List continued on next page.)

*Primary Examiner*—Jeffrey Fredman
*Attorney, Agent, or Firm*—Charles B. Cappellari; Carlos A. Fisher

[57] ABSTRACT

The present invention discloses hybridization assay probes, amplification primers, nucleic acid compositions and methods useful for detecting Neisseria nucleic acids. Hybridization assay probes and amplification primers that selectively detect *Neisseria meningitidis* and distinguish those *Neisseria meningitidis* from *Neisseria gonorrohoeae* are disclosed. Other hybridization probes selectively detect *Neisseria gonorrohoeae* and not *Neisseria meningitidis* are also described.

18 Claims, No Drawings

OTHER PUBLICATIONS

Ni et al., "Polymerase chain reaction for diagnosis for meningococcal meningitis," *Lancet* 340:1432–1434 (1992).

Radstrom et al., "Detection of bacterial DNA in cerebrospinal fluid by an assay for simultaneous detection of *Neisseria meningitidis*, *Haemophilus influenzae*, and Streptococci using a seminested PCR strategy," *J. Clin. Microbiol.* 32(11):2738–2744 (1994).

Rossau et al., "Nucleotide sequence of a 16S ribosomal RNA gene from *Neisseria gonorrhoea*," *Nucleic Acids Research* 16(13):6227 (1988).

Rossau et al., "Evaluation of an rRNA–Derived Oligonucleotide Probe for Culture Confirmation of *Neisseria gonorrhoeae*," *J. Clin. Microbiol.* 28:944–948 (1990).

Sambrook et al., "Ch. 11," in *Molecular Cloning: A Laboratory Manual, 2nd Edition*, Cold Spring Harbor Laboratory Press, (1989).

Southern, "Detection of Specific Sequences Among DNA Fragments Seperated by Gel Electrophoresis," *J. Mol. Biol.* 98:503–517 (1975).

Wolff et al., "Phylogeny and nucleotide sequence of a 23S rRNA gene from *Neisseria gonorrhoeae* and *Neisseria meningitidis*," *Nucleic Acids Research* 20(17):4657 (1992).-

NUCLEIC ACID PROBES AND AMPLIFICATION OLIGONUCLEOTIDES FOR NEISSERIA SPECIES

This is a continuation of application Ser. No. 08/484,607 filed Jun. 7, 1995 now U.S. Pat. No. 5,747,252, hereby incorporated by reference in its totality (including drawings).

FIELD OF THE INVENTION

The inventions described and claimed herein relate to the design and use of amplification oligonucleotides and nucleic acid probes to *Neisseria gonorrhoeae* and *Neiseria meningitidis* which allow detection of these organisms in test samples.

BACKGROUND OF THE INVENTION

The genus Neisseria includes two gram-negative species of pyogenic cocci that are pathogenic for man, and that have no other known reservoir: the meningococcus (*Neisseria meningitidis*) and the gonococcus (*Neisseria gonorrhoeae*). A number of non-pathogenic species also inhabit the upper respiratory tract of humans and may be easily confused with meningococci. *Meningococcal meningitis* was recognized as a contagious disease early in the 19th century and is especially prevalent among military personnel. The causative agent of meningococcal meningitis is *Neisseria meningitidis.*

*Neisseria gonorrhoeae* is one of the main causes of epidemic sexually transmitted disease and is prevalent in the United States. Infection with *Neisseria gonorrhoeae* causes many common symptoms including urethritis, cervicitis, and proctitis. In addition, chronic infection with *Neisseria gonorrhoeae* can cause pelvic inflammatory disease.

Meningococci have polysaccharide-containing capsules. Gonococcis may also possess capsules, but the exact chemical composition of such a capsule is unknown. In addition, both gonococci and meningococci may have pili which play a role in virulence.

Meningococci and gonococci are difficult to cultivate and require special techniques to grow the organisms from body fluids. In addition, selective culture medium, (for example, Thayer-Martin medium) and growth in 3–10% carbon dioxide at approximately 35° C. is required to maximize the culture of organisms.

In addition to the difficult cultivation, the gonococcus and meningococcus detection by immunoassay suffers a lack of sensitivity and specificity. This appears to be due to the cross reaction between various other pathogens and non-pathogenic microorganisms often found in the same clinical specimens.

Oligonucleotides for the amplification of nucleic acid for detection of Neisseria have been described. Bikenmeyer and Armstrong, *J. Clin. Microbiol.* 30:3089–3094 (1992), describe probe sets for use in the ligase chain reaction directed to the Opa and pilin genes of *Neisseria gonorrhoeae.* Kristiansen et al. *Lancet* 340:1432–1434 (1992) describe primers directed to an insertion element referred to as IS1106 for amplification and detection of *Neisseria meningitidis.* McLaughlin et al., *Mol. and Cell Probes* 7:7–17 (1993) describe primers for use in the polymerase chain reaction directed to the 16S-23S rRNA internal transcribed spacer and a set of primers directed to a subregion of the 16S rRNA of *Neisseria meningitidis.* Probes for the detection of rRNA or rDNA sequences of *Neisseria gonorrhoeae* and/or *Neisseria meningitidis* have been described by Granato and Franz *J. Clin. Microbiol.* 28:944–948, (1990), Wolff, U.S. Pat. No. 5,173,401 (Dec. 22, 1992), Rossau and Van Heuverswijn, European Patent Application Publication No. 0 337 896, Hogan et al. PCT/US87/03009, and Barns et al., U.S. Pat. No. 5,217,862 (Jun. 8, 1993).

SUMMARY OF INVENTION

The featured invention discloses and claims novel and useful amplification oligonucleotides, helper oligonucleotides, and oligonucleotide hybridization assay probes which are designed to be complementary to specific regions of the rRNA (ribosomal RNA) or rDNA (ribosomal DNA) nucleotide sequences of Neisseria, or oligonucleotides having a nucleic acid sequence substantially corresponding to a specific portion of Neisseria rRNA or rDNA nucleotide sequence or its complement. Because these amplification oligonucleotides, helper oligonucleotides and hybridization assay probes are derived from the rRNA of pathogenic Neisseria, a superior detection assay is obtained due to the higher level of RNA expressed from these rRNA genes and the lack of lateral transfer of the rRNA sequences between organisms.

The amplification oligonucleotides and oligonucleotide hybridization assay probes function by hybridizing to target Neisseria 16S and 23S rRNA and/or rDNA gene sequences under stringent hybridization assay conditions. In preferred embodiments, the probes and amplification oligonucleotides described herein, when used together, can distinguish *Neisseria meningitidis* from other microorganisms found in clinical samples such as blood or tissues and from *Neisseria gonorrhoeae* species. Accordingly, the amplification oligonucleotides and hybridization assay probes may be used in an assay to specifically detect and/or amplify *Neisseria meningitidis*-derived nucleic acids. In preferred embodiments, the hybridization assay probes described herein are able to selectively hybridize to nucleic acids from *Neisseria meningitidis* over those from *Neisseria gonorrhoeae* under stringent hybridization conditions. In some embodiments of the present invention, the hybridization assay probe comprises an oligonucleotide that contains a reporter group such as an acridinium ester or a radioisotope to help identify hybridization of the probe to its target sequence. In some embodiments of the present invention, the amplification oligonucleotide optionally has a nucleic acid sequence recognized by an RNA polymerase or which enhances transcription initiation by an RNA polymerase.

The present invention features hybridization assay probes useful for detecting the presence of nucleic acids from Neisseria. Preferably, the hybridization assay probes are selected from the following nucleotide sequences:

SEQ ID NO 11: GGCTGTTGCT AATATCAGCG
SEQ ID NO 12: GGCTGTTGCT AATACCAGCG
SEQ ID NO 15: CGCTGATATT AGCAACAGCC
SEQ ID NO 16: CGCTGGTATT AGCAACAGCC
SEQ ID NO 25: GGCUGUUGCU AAUAUCAGCG
SEQ ID NO 26: GGCUGUUGCU AAUACCAGCG
SEQ ID NO 27: CGCUGAUAUU AGCAACAGCC
SEQ ID NO 28: CGCUGGUAUU AGCAACAGCC
SEQ ID NO 1: GAACGTACCG GGTAGCGG
SEQ ID NO 3: GCCAATATCG GCGGCCGATG
SEQ ID NO 29: CCGCTACCCG GTACGTTC
SEQ ID NO 30: CATCGGCCGC CGATATTGGC
SEQ ID NO 31: GAACGUACCG GGUAGCGG
SEQ ID NO 32: GCCAAUAUCG GCGGCCGAUG
SEQ ID NO 33: CCGCUACCCG GUACGUUC
SEQ ID NO 34: CAUCGGCCGC CGAUAUUGGC

The present invention features hybridization assay probes useful for detecting nucleic acids from *Neisseria meningitidis*. These hybridization assay probes are preferably selected from the following nucleotide sequences:

SEQ ID NO: 11 GGCTGTTGCT AATATCAGCG

SEQ ID NO: 12 GGCTGTTGCT AATACCAGCG

SEQ ID NO: 15 CGCTGATATT AGCAACAGCC

SEQ ID NO: 16 CGCTGGTATT AGCAACAGCC

SEQ ID NO: 25 GGCUGUUGCU AAUAUCAGCG

SEQ ID NO: 26 GGCUGUUGCU AAUACCAGCG

SEQ ID NO: 27 CGCUGAUAUU AGCAACAGCC, and

SEQ ID NO: 28 CGCUGGUAUU AGCAACAGCC.

The present invention also features hybridization assay probes useful for detecting *Neisseria gonorrhoeae* nucleic acids. Preferably, these hybridization assay probes have a nucleotide sequence selected from one of the following nucleotide sequences:

SEQ ID NO: 1 GAACGTACCG GGTAGCGG

SEQ ID NO: 3 GCCAATATCG GCGGCCGATG

SEQ ID NO: 29 CCGCTACCCG GTACGTTC

SEQ ID NO: 30 CATCGGCCGC CGATATTGGC

SEQ ID NO: 31 GAACGUACCG GGUAGCGG

SEQ ID NO: 32 GCCAAUAUCG GCGGCCGAUG

SEQ ID NO: 33 CCGCUACCCG GUACGUUC, and

SEQ ID NO: 34 CAUCGGCCGC CGAUAUUGGC.

Another aspect of the present invention is a probe mix comprising a hybridization assay probe of the present invention together with a helper oligonucleotide (probe). Preferably, helper oligonucleotides are used to facilitate the specific hybridization of the assay probe to its target nucleic acid; helper oligonucleotides are described by Hogan and Milliman U.S. Pat. No. 5,030,557 which is hereby incorporated by reference and enjoys common ownership with the present invention. Oligonucleotides used as helper probes in this invention include the following sequences:

SEQ ID NO: 2 GGGATAACTG ATCGAAAGAT CAGCTAATAC CGCATACG

SEQ ID NO: 4 ACGGTACCTG AAGAATAAGC ACCG-GCTAAC TACGTG

SEQ ID NO: 39 GGGAUAACUG AUCGAAAGAU CAGCUAAUAC CGCAUACG

SEQ ID NO: 40 ACGGUACCUG AAGAAUAAGC ACCGGCUAAC UACGUG

SEQ ID NO: 13 GCCTTCGGGT TGTAAAGGAC TTTTGTCAGG GAAGAAAA

SEQ ID NO: 14 GCTGATGACG GTACCTGAAG AATAAGCACC GGC

SEQ ID NO: 35 GCCUUCGGGU UGUAAAGGAC UUUUGUCAGG GAAGAAAA

SEQ ID NO: 36 GCUGAUGACG GUACCUGAAG AAUAAGCACC GGC

SEQ ID NO: 17 TTTTCTTCCC TGACAAAAGT CCTT-TACAAC CCGAAGGC

SEQ ID NO: 18 GCCGGTGCTT ATTCTTCAGG TAC-CGTCATC AGC

SEQ ID NO: 37 UUUUCUUCCC UGACAAAAGU CCU-UUACAAC CCGAAGGC, and

SEQ ID NO: 38 GCCGGUGCUU AUUCUUCAGG UAC-CGUCAUC AGC

Another aspect of the present invention includes compositions for detecting *Neisseria meningitidis* and *Neisseria gonorrhoeae* that are nucleic acid hybrids formed between an oligonucleotide of the present invention and a specific region of a nucleotide polymer from a *Neisseria meningitidis* or *Neisseria gonorrhoeae*. Generally, the nucleotide polymer contains a nucleic acid sequence that substantially corresponds to an oligonucleotide sequence of the present invention or its complement and is derived from the rRNA or the rDNA encoding the ribosomal RNA of the *Neisseria meningitidis* or *Neisseria gonorrhoeae*. The oligonucleotide present in these compositions may be an amplification oligonucleotide, a helper oligonucleotide, a hybridization assay probe, or a combination thereof. Thus, compositions of the present invention may contain one or more amplification oligonucleotides, one or more helper oligonucleotides, and one or more hybridization assay probes.

The compositions of the present invention containing a probe hybridized to its target sequence are useful for detecting the presence of a nucleic acid sequence. Compositions of the present invention containing a helper oligonucleotide hybridized to its target nucleic acid sequence are useful for making a particular portion of the target nucleic acid available for hybridization. Compositions of the present invention containing an oligonucleotide primer hybridized to its target sequence are useful for creating an initiation site for a polymerase at the 3' end of the primer, and/or providing a template for extension of the 3' end of the target sequence.

The present invention also contemplates methods for detecting the presence of Neisseria in which a test sample is contacted with a nucleic acid hybridization assay probe under stringent hybridization assay conditions wherein the nucleic acid hybridization assay probe is capable of hybridizing to *Neisseria meningitidis* target nucleic acid sequences and not to the nucleic acid sequences from *Neisseria gonorrhoeae*. The present invention also contemplates oligonucleotides and the equivalents thereof used in these methods that optionally contain a reporter molecule that aids in the identification of the hybridization of the probe to its target sequence. This invention is useful for detecting the presence of Neisseria nucleic acids in test samples from humans such as blood, blood derived samples, tissues, tissue derived samples, other body fluids and body samples.

The present invention also contemplates methods for detecting the presence of *Neisseria meningitidis* in which the nucleic acid is amplified using at least one amplification oligonucleotide of the present invention. In preferred embodiments, that amplification is then followed by a detection step in which the amplified nucleic acid is detected using an oligonucleotide hybridization assay probe of the present invention. The methods of the present invention also contemplate the use of amplification oligonucleotides which include the nucleotide sequence for an RNA promoter.

In another aspect, the invention features amplification oligonucleotides useful for detection of organisms of the genus Neisseria in an amplification assay. Such oligomers preferably substantially correspond to one of the following nucleotide sequences:

SEQ ID NO: 5 GTCCCCTGCT TTCCCTCTCA AGAC

SEQ ID NO: 6 GGCGAGTGGC GAACGGGTGA GTAA-CATA

SEQ ID NO: 7 GCTGCTGCAC GTAGTTAGCC GGT-GCTTATT CTTCAG

SEQ ID NO: 8 GTTAGCCGGT GCTTATTCTT CAGG-TACCGT CATCG

SEQ ID NO: 9 CGGGTTGTAA AGGACTTTTG TCAGG-GAAGA AAAGGCCGTT

SEQ ID NO: 10 GAAGGCCTTC GGGTTGTAAA GGAC

SEQ ID NO: 41 GUCCCCUGCU UUCCCUCUCA AGAC

SEQ ID NO: 42 GGCGAGUGGC GAACGGGUGA GUAACAUA

SEQ ID NO: 43 GCUGCUGCAC GUAGUUAGCC GGUGCUUAUU CUUCAG

SEQ ID NO: 44 GUUAGCCGGU GCUUAUUCUU CAG-GUACCGU CAUCG

SEQ ID NO: 45 CGGGUUGUAA AGGACUUUUG UCAGGGAAGA AAAGGCCGUU, and

SEQ ID NO: 46 GAAGGCCUUC GGGUUGUAAA GGAC where the oligomer may be unmodified or contain a modification such as addition of a specific nucleic acid sequence to 5' terminus that is recognized by an RNA polymerase, (including but not limited to the promoter sequence for T7, T3, or SP6 RNA polymerase), and/or sequences which enhance initiation of RNA transcription by an RNA polymerase. One example of a promoter sequence includes the sequence SEQ ID NO. 53 5'-AATTTAATACGACTCACTATAGGGAGA-3'. Other examples of useful promoter sequences are contained in various commercially available vectors including, for example, pBluescript® vectors from Stratagene Cloning Systems (San Diego, Calif.) or the pGEM™ vectors from Promega Corp. (Madison, Wis.)

In another aspect of the present invention the amplification oligonucleotides bind to or cause elongation through sequences substantially corresponding to the following sequences:

SEQ ID NO: 23 GTCTTGAGAG GGAAAGCAGG GGAC

SEQ ID NO: 24 TATGTTACTC ACCCGTTCGC CACTCGCC

SEQ ID NO: 19 CTGAAGAATA AGCACCGGCT AACTACGTGC AGCAGC

SEQ ID NO: 21 CGATGACGGT ACCTGAAGAA TAAGCACCGG CTAAC

SEQ ID NO: 20 AACGGCCTTT TCTTCCCTGA CAAAAGTCCT TTACAACCCG

SEQ ID NO: 22 GTCCTTTACA ACCCGAAGGC CTTC

SEQ ID NO: 47 GUCUUGAGAG GGAAAGCAGG GGAC

SEQ ID NO: 48 UAUGUUACUC ACCCGUUCGC CACUCGCC

SEQ ID NO: 49 CUGAAGAAUA AGCACCGGCU AACUACGUGC AGCAGC

SEQ ID NO: 50 CGAUGACGGU ACCUGAAGAA UAAGCACCGG CUAAC

SEQ ID NO: 51 AACGGCCUUU UCUUCCCUGA CAAAAGUCCU UUACAACCCG

SEQ ID NO: 52 GUCCUUUACA ACCCGAAGGC CUUC

Another aspect of the present invention includes kits that contain one or more of the oligonucleotides of the present invention including amplification oligonucleotides, helper oligonucleotides and hybridization assay probes. In preferred embodiments, a kit of the present invention includes at least one amplification oligonucleotide and one hybridization assay probe capable of distinguishing Neisseria, *Neisseria meningitidis* or *Neisseria gonorrhoeae* from other microorganisms.

Background descriptions of the use of nucleic acid hybridization to detect particular nucleic acid sequences are given in Kohne, U.S. Pat. No. 4,851,330 issued Jul. 25, 1989, and by Hogan et al., International Patent Application No. PCT/US87/03009, entitled "Nucleic Acid Probes for Detection and/or Quantitation of Non-Viral Organisms", both references hereby incorporated by reference herein. Hogan et al., supra, describe methods for determining the presence of a non-viral organism or a group of non-viral organisms in a sample (e.g., sputum, urine, blood and tissue sections, food, soil and water).

In the most preferred embodiments, the compositions, probe mixes, probes, amplification primers, helper oligonucleotides and the like have a nucleotide sequence that consists of the specified nucleic acid sequence rather than substantially corresponding to the nucleic acid sequence. These most preferred embodiments use the sequence listed in the sequence listing which forms part of the present disclosure.

DETAILED DESCRIPTION OF THE INVENTION

A. Definitions

The following terms have the indicated meanings in the specification unless expressly indicated to have a different meaning.

By "target nucleic acid" is meant a nucleic acid having a target nucleotide sequence.

By "oligonucleotide" is meant a single-stranded nucleotide polymer made of more than 2 nucleotide subunits covalently joined together. Preferably between 10 and 100 nucleotide units are present, most preferably between 12 and 50 nucleotides units are joined together. The sugar groups of the nucleotide subunits may be ribose, deoxyribose or modified derivatives thereof such as 2'-O-methyl ribose. The nucleotide subunits of an oligonucleotide may be joined by phosphodiester linkages, phosphorothioate linkages, methyl phosphonate linkages or by other rare or non-naturally-occurring linkages that do not prevent hybridization of the oligonucleotide. Furthermore, an oligonucleotide may have uncommon nucleotides or non-nucleotide moieties. An oligonucleotide as defined herein is a nucleic acid, preferably DNA, but may be RNA or have a combination of ribo- and deoxyribonucleotides covalently linked. Oligonucleotide probes and amplification oligonucleotides of a defined sequence may be produced by techniques known to those of ordinary skill in the art, such as by chemical or biochemical synthesis, and by in vitro or in vivo expression from recombinant nucleic acid molecules, e.g., bacterial or retroviral vectors. As intended by this disclosure, an oligonucleotide does not consist of wild-type chromosomal DNA or the in vivo transcription products thereof. One use of a probe is as a hybridization assay probe; probes may also be used as in vivo or in vitro therapeutic amplification oligomers or antisense agents to block or inhibit gene transcription, or translation in diseased, infected, or pathogenic cells.

By "target nucleic acid sequence", "target nucleotide sequence" or "target sequence" is meant a specific deoxyribonucleotide or ribonucleotide sequence comprising all or a part of the nucleotide sequence of a single-stranded nucleic acid molecule, and the deoxyribonucleotide or ribonucleotide sequence complementary thereto.

Nucleic acid hybridization is the process by which two nucleic acid strands having completely or partially complementary nucleotide sequences come together under predetermined reaction conditions to form a stable, double-stranded hybrid with specific hydrogen bonds. Either nucleic acid strand may be a deoxyribonucleic acid (DNA), a ribonucleic acid (RNA), or an analog of one of these nucleic acids; thus hybridization can involve RNA:RNA hybrids, DNA:DNA hybrids, or RNA:DNA hybrids.

The term "hybridization" as used in this application, refers to the ability of two completely or partly complementary single nucleic acid strands to come together in an antiparallel orientation to form a stable structure having a double-stranded region. The two constituent strands of this double-stranded structure, sometimes called a hybrid, are held together with hydrogen bonds. Although these hydrogen bonds most commonly form between nucleotides containing the bases adenine and thymine or uracil (A and T or U) or cytosine and guanine (C and G) on single nucleic acid strands, base pairing can form between bases who are not members of these "canonical" pairs. Non-canonical base pairing is well-known in the art. See e.g., *The Biochemistry of the Nucleic Acids* (Adams et al., eds., 1992).

"Stringent" hybridization assay conditions refer to conditions wherein a specific hybridization assay probe is able to hybridize with target nucleic acids (preferably rRNA or rDNA of a Neisseria, *Neisseria meningitidis* or *Neisseria gonorrhoeae*) over other nucleic acids present in the test sample derived either from other microorganisms or from humans. It will be appreciated that these conditions may vary depending upon factors including the GC content and length of the probe, the hybridization temperature, the composition of the hybridization reagent or solution, and the degree of hybridization specificity sought. Specific stringent hybridization conditions are provided in the disclosure below.

As an example of specific stringent hybridization conditions useful in detecting Neisseria, *Neisseria meningitidis* or *Neisseria gonorrhoeae,* for the hybridization assay probes of this invention, a set of preferred stringent hybridization assay conditions was used. One preferred set comprised hybridizing the target nucleic acid and hybridization probe together in 100 $\mu$l of 0.05 M lithium succinate (pH 5.0), 6 M LiCl, 1% (w/v) lithium lauryl sulfate, (L.L.S.) 10 mM ethylene diamine tetraacetic acid (EDTA), 10 mM ethylene glycol bis (β-amino ethyl ether) N,N,N',N' tetraacetic acid (EGTA) at 60° C. for 15 minutes, then adding 300 $\mu$l of 0.15 M sodium tetraborate (pH 8.5), 1% (v/v) TRITON® X-100 at 60° C. for 5–7 minutes. Additional sets of stringent hybridization conditions can be determined after reading the present disclosure by those or ordinary skill in the art.

By "probe" is meant a single-stranded oligonucleotide having a sequence partly or completely complementary to a nucleic acid sequence sought to be detected, so as to hybridize thereto under stringent hybridization conditions. The term "probe" is meant to exclude nucleic acids normally existing in nature. Purified oligonucleotide probes may be produced by techniques known in the art such as chemical synthesis and by in vitro or in vivo expression from recombinant nucleic acid molecules, e.g., retroviral vectors. Preferably probes are 10 to 100 nucleotides in length. Probes may or may not have regions which are not complementary to a target sequence, so long as such sequences do not substantially affect hybridization under stringent hybridization conditions. If such regions exist they may contain a 5' promoter sequence and/or a binding site for RNA transcription, a restriction endonuclease recognition site, or may contain sequences which will confer a desired secondary or tertiary structure, such as a catalytic active site or a hairpin structure on the probe, on the target nucleic acid, or both. A probe may be labeled with a reporter group moiety such as a radioisotope, a fluorescent or chemiluminescent moiety, with an enzyme or ligand, which can be used for detection or confirmation that the probe has hybridized to the target sequence.

As used in this disclosure, the phrase "a probe (or oligonucleotide) having a nucleic acid sequence consisting essentially of a sequence selected from" a group of specific sequences means that the probe, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

The phrase "substantially corresponding to a nucleic acid sequence" means that the referred-to nucleic acid is sufficiently similar to the nucleic acid sequence such that the referred-to nucleic acid has similar hybridization properties to a nucleic acid sequence in that it would hybridize with the same target nucleic acid sequences under stringent hybridization conditions.

One skilled in the art will understand that substantially corresponding probes and primers of the invention can vary from the referred-to sequence and still hybridize to the same target nucleic acid sequence. This variation from the nucleic acid may be stated in terms of a percentage of identical bases within the sequence or the percentage of perfectly complementary bases between the probe or primer and its target sequence. One skilled in the art will also understand that this variation could be expressed as the number of bases in a probe or primer or the number of mismatched bases of a probe that do not hybridize to a corresponding base of a target nucleic acid sequence. Probes or primers of the present invention substantially correspond to a nucleic acid sequence if these percentages are from 100% to 80% or from 0 base mismatches in a 10 nucleotide target sequence to 2 bases mismatched in a 10 nucleotide target sequence.

In preferred embodiments, the percentage is from 100% to 85%. In more preferred embodiments, this percentage is from 90% to 100%; in other preferred embodiments, this percentage is from 95% to 100%. One skilled in the art will understand the various modifications to the hybridization conditions that might be required at various percentages of complementarity to allow hybridization to a specific target sequence without causing an unacceptable level of non-specific hybridization.

By "nucleic acid hybrid" or "hybrid" is meant a nucleic acid structure containing a double-stranded, hydrogen-bonded region, preferably of between 10 and 100 nucleotides in length, most preferably of between about 12 and 50 nucleotides in length, wherein each strand is complementary to the other and wherein the region is sufficiently stable under stringent hybridization conditions to be detected by means including but not limited to chemiluminescent or fluorescent light detection, autoradiography, or gel electrophoresis. Such hybrids may comprise RNA:RNA, RNA:DNA, or DNA:DNA duplex molecules or duplex molecules containing analogs of these nucleic acids.

By "complementary" is meant that the nucleotide sequences of similar regions of two single-stranded nucleic acids, or to different regions of the same single-stranded nucleic acid have a nucleotide base composition that allow the single strands to hybridize together in a stable double-stranded hydrogen-bonded region under stringent hybridization conditions. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "perfectly" complementary.

By "conservatively modified variants" is meant nucleic acids or oligonucleotides having a nucleotide sequence that is complementary to a nucleic acid region of another nucleic acid, such region in turn being perfectly complementary to a reference nucleic acid. Such conservatively modified variants are able to stably hybridize to a target nucleic acid region having a Neisseria, *Neisseria meningitidis* or *Neisseria gonorrhoeae* nucleotide sequence under stringent hybridization conditions.

By "amplification oligonucleotide" is meant an oligonucleotide capable of hybridizing to a target nucleic acid sequence and acting as a primer for nucleic acid synthesis or a promoter template (e.g., for synthesis of a complementary strand, thereby forming a functional promoter sequence), or both, for the initiation of nucleic acid synthesis. If the amplification oligonucleotide is designed to initiate RNA synthesis, the oligonucleotide may contain nucleotide sequences which are non-complementary to the target sequence, but are recognized by an RNA polymerase (such as T7, T3 and SP6 RNA polymerase). An amplification oligonucleotide may or may not have a 3' terminus which is modified to prevent or lessen the amount of primer extension. An amplification oligonucleotide as defined herein will preferably be between 10 and 100 nucleotides in length; most preferably between about 12 and 50 nucleotides in length. While the amplification oligonucleotides of the present invention may be chemically synthesized or derived from a vector, such oligonucleotides are not naturally-occurring nucleic acids.

By “nucleic acid amplification” or “target amplification” is meant increasing the number of nucleic acid molecules having at least one target nucleic acid sequence.

By “antisense” or “negative sense” is meant having a nucleic sequence complementary to that of a reference nucleic acid sequence.

By “sense”, “same-sense” or “positive sense” is meant having a nucleic acid sequence analogous to that of a reference nucleic acid sequence.

By “helper oligonucleotide” is meant a nucleic acid probe designed to hybridize with the target nucleic acid at a different locus than that of a labeled probe, thereby either increasing the rate of hybridization of the labeled probe, increasing the melting temperature (Tm) of the target:labeled probe hybrid, or both.

“Phylogenetically closely related” means that the organisms are closely related to each other in an evolutionary sense and therefore would have a higher total nucleic acid sequence homology than organisms that are more distantly related. Organisms occupying adjacent and next to adjacent positions on the phylogenetic tree are closely related. Organisms occupying positions further away than adjacent or next to adjacent positions on the phylogenetic tree will still be closely related if they have significant total nucleic acid sequence homology.

B. Hybridization Conditions and Probe/Primer Design

Hybridization reaction conditions, most importantly the temperature of hybridization and the concentration of salt in the hybridization solution, can be selected to allow the amplification oligonucleotides or hybridization probes of the present invention to preferentially hybridize to nucleic acids having a target Neisseria nucleotide sequence, and not to other non-target nucleic acids suspected of being present in the test sample. At decreased salt concentrations and/or increased temperatures (called increased stringency) the extent of nucleic acid hybridization decreases as hydrogen bonding between paired nucleotide bases in the double-stranded hybrid molecule is disrupted; this process is called “melting”.

Generally speaking, the most stable hybrids are those having the largest number of contiguous perfectly matched (i.e., hydrogen-bonded) nucleotide base pairs. Thus, such hybrids would usually be expected to be the last to melt as the stringency of the hybridization conditions increases. However, a double-stranded nucleic acid region containing one or more mismatched, “non-canonical”, or imperfect base pairs (resulting in weaker or non-existent base pairing at that position in the nucleotide sequence of a nucleic acid) may still be sufficiently stable under conditions of relatively high stringency to allow the nucleic acid hybrid to be detected in a hybridization assay without cross reacting with other, non-selected nucleic acids present in the test sample.

Hence, depending on the degree of similarity between the nucleotide sequences of the target nucleic acid and those of non-target nucleic acids belonging to phylogenetically distinct, but closely-related organisms on one hand, and the degree of complementarity between the nucleotide sequences of a particular amplification oligonucleotide or hybridization probe and those of the target and non-target nucleic acids on the other, one or more mismatches will not necessarily defeat the ability of the oligonucleotide to hybridize to that nucleic acid and not to non-target nucleic acids.

The hybridization assay probes of the present invention were chosen, selected, and/or designed to maximize the difference between the melting temperatures of the probe:target hybrid (Tm, defined as the temperature at which half of the potentially double-stranded molecules in a given reaction mixture are in a single-stranded, denatured state) and the Tm of a mismatched hybrid formed between the probe and the rRNA or rDNA of the phylogenetically most closely-related organisms expected to be present in the test sample, but not sought to be detected. While the unlabeled amplification oligonucleotides and helper oligonucleotides need not have such an extremely high degree of specificity as the labeled hybridization assay probe to be useful in the present invention, they are designed in a similar manner to preferentially hybridize to one or more target nucleic acids over other nucleic acids.

Probes specific for *Neisseria meningitidis* were designed using sequences determined in prospective target areas using primers complementary to the 16S rRNAs of strains of Neisseria including *Neisseria gonorrhoeae* (ATCC No. 19424), *Neisseria meningitidis* serogroup A (ATCC No. 13077), serogroup C (ATCC No. 23248) and serogroup L (ATCC No. 43828), clinical isolates of *Neisseria meningitidis, Neisseria lactamica* (ATCC NO. 29193), *Neisseria cinerea* (ATCC NO. 14685), *Neisseria mucosa* (ATCC NO. 19696), *Neisseria sicca* (ATCC NO. 29193) and *Kingella kingae* (ATCC No. 23330). The nucleic acid sequence from phylogenetically near neighbors, including the published sequence of *Neisseria gonorrhoeae* NCTC 8375, Rossau et al. *Nuc. Acids Res.* 16:6227 were also used as comparisons with the nucleic sequences from *Neisseria meningitidis* to determine variable regions.

To facilitate the identification of nucleic acid sequences to be used as probes and amplification oligonucleotides, the nucleotide sequences from different species of organisms were first aligned to maximize homology. Within the rRNA molecule there is a close relationship between the overall structure and function. This imposes restrictions on evolutionary changes in the primary sequence so that the secondary structure is maintained. For example, if a base is changed on one side of a helix, a compensating change may be evolutionarily made to the other side to preserve the complementarity (this is referred to as co-variance). This allows two very different sequences to be aligned using the conserved primary sequence and also the conserved secondary structure elements as points of reference. Potential target sequences for the hybridization probes were identified by noting variations in the homology of the aligned sequences in certain discrete regions (variable regions) of the rRNA and rDNA sequences.

The sequence evolution at each of the variable regions is mostly divergent. Because of the divergence, more distant phylogenetic relatives of *Neisseria meningitidis* or *Neisseria gonorrhoeae* tend to show greater variability in a given variable region than phylogenetically closer relatives. The observed sufficient variation between *Neisseria meningitidis* and *Neisseria gonorrhoeae* species was used to identify preferred target sites and design useful probes.

We have identified sequences which vary between *Neisseria meningitidis* and *Neisseria gonorrhoeae,* between these and other Neisseria species, and between members of the genus Neisseria and other organisms by comparative analysis of rRNA sequences published in the literature or determined in the laboratory. Computers and computer programs which may be used or adapted for the purposes herein disclosed are commercially available. We have seen sufficient variation between the target organisms and the closest phylogenetic relative likely to be found in the same sample to design the present probes. The *Neisseria meningitidis* strains have been classified into three sequence groups in the probe region represented by serogroups A, C and L.

Merely identifying putatively unique potential target nucleotide sequences does not guarantee that a functionally species-specific hybridization assay probe may be made to hybridize to Neisseria rRNA or rDNA comprising that sequence. Various other factors will determine the suitability of a nucleic acid locus as a target site for species-specific probes. Because the extent and specificity of hybridization reactions such as those described herein are affected by a number of factors, manipulation of one or more of those factors will determine the exact sensitivity and specificity of a particular oligonucleotide, whether perfectly complementary to its target or not. The importance and effect of various assay conditions are known to those skilled in the art as described in Hogan et al., PCT/US87/03009, and Hogan and Hammond, U.S. Pat. No. 5,216,143, and Kohne, U.S. Pat. No. 4,851,330 which share the same assignee as the present application and are hereby incorporated by reference herein.

The desired temperature of hybridization and the hybridization solution composition (such as salt concentration, detergents and other solutes) can also greatly affect the stability of double-stranded hybrids. Conditions such as ionic strength and the temperature at which a probe will be allowed to hybridize to target must be taken into account in constructing a group- or species-specific probe. The thermal stability of hybrid nucleic acids generally increases with the ionic strength of the reaction mixture. On the other hand, chemical reagents which disrupt hydrogen bonds, such as formamide, urea, dimethyl sulfoxide and alcohols, can greatly reduce the thermal stability of the hybrids.

To maximize the specificity of a probe for its target, the subject probes of the present invention were designed to hybridize with their targets under conditions of high stringency. Under such conditions only single nucleic acid strands having a high degree of complementarity will hybridize to each other; single nucleic acid strands without such a high degree of complementarity will not form hybrids. Accordingly, the stringency of the assay conditions determines the amount of complementarity which should exist between two nucleic acid strands in order to form a hybrid. Stringency is chosen to maximize the difference in stability between the hybrid formed between the probe and the target nucleic acid and potential hybrids between the probe and any non-target nucleic acids present.

Proper specificity may be achieved by minimizing the length of the probe having perfect complementarity to sequences of non-target organisms, by avoiding G and C rich regions of homology to non-target sequences, and by constructing the probe to contain as many destabilizing mismatches to nontarget sequences as possible. Whether a probe sequence is useful to detect only a specific type of organism depends largely on the thermal stability difference between probe:target hybrids versus potential probe:nontarget hybrids. In designing probes, the differences in the Tm values between these hybrids should be made as large as possible (preferably about 5° C. or more). Manipulation of the Tm can be accomplished by changes to probe length and probe composition (GC content vs. AT content).

In general, the optimal hybridization temperature for oligonucleotide probes of about 10–50 nucleotides in length is approximately 5° C. below the melting temperature for a given duplex. Incubation at temperatures below the optimum temperature may allow mismatched base sequences to hybridize and can therefore decrease specificity. The longer the probe, the more hydrogen bonding between base pairs and, in general, the higher the Tm. Increasing the percentage of G and C also increases the Tm because G-C base pairs exhibit additional hydrogen bonding and therefore greater thermal stability than A-T base pairs.

A preferred method to determine Tm measures hybridization using a Hybridization Protection Assay (HPA) according to Arnold et al., U.S. Pat. No. 5,283,174 which enjoys exclusive ownership with the present application and is incorporated by reference herein. Tm can be measured using HPA in the following manner. A probe:target hybrid is formed in lithium succinate buffered solution (0.1 M lithium succinate buffer, pH 5.0, 2 mM ethylenediamine tetraacetic acid (EDTA), 2 mM ethylene glycol-bis(β-amino-ethyl ether) N,N,N', N'-tetraacetic acid (EGTA), 10% (w/v) lithium lauryl sulfate) using an excess amount of target. Aliquots of the hybrid are then diluted in the lithium succinate buffered solution and incubated for five minutes at various temperatures starting below that of the anticipated Tm for example, 55° C. and increasing in 2–5° C. increments. This solution is then diluted with a mild alkaline borate buffer (0.15 M sodium tetraborate, pH 7.6, 5% (v/v) TRITON® X-100) and incubated at a lower temperature (for example 50° C.) for ten minutes. Under these conditions the acridinium ester attached to a single-stranded probe is hydrolyzed while the acridinium ester attached to hybridized probe is relatively protected from hydrolysis. Thus, the amount of acridinium ester remaining is proportional to the amount of hybrid and can be measured by the chemiluminescence produced from the acridinium ester upon the addition of hydrogen peroxide followed by alkali. Chemiluminescence can be measured in a luminometer (e.g., Gen-Probe LEADER® I or LEADER® 50). The resulting data are plotted as percent of maximum signal (usually from the lowest temperature) versus temperature. The Tm is defined as the temperature at which 50% of the maximum signal remains. In addition to the method above, Tm may be determined by isotopic methods well known to those skilled in the art (e.g., Hogan et al., supra).

It should be noted that the Tm for a given hybrid varies depending on the hybridization solution used. Factors such as the salt concentration, detergents, and other solutes can effect hybrid stability during thermal denaturation (J. Sambrook, E. F. Fritsch and T. Maniatis, 2 *Molecular Cloning,* ch. 11 (2d ed. 1989)). Conditions such as ionic strength and incubation temperature under which a probe will be used to hybridize to target should be taken into account in constructing a probe. On the other hand, chemical reagents which disrupt hydrogen bonds such as formamide, urea, dimethylsulfoxide and alcohols, can greatly reduce the thermal stability of the hybrids.

To ensure the probe is specific for its target, it is desirable to have probes which hybridize only under conditions of high stringency. Under conditions of high stringency only highly complementary nucleic acid hybrids will form; hybrids without a sufficient degree of complementarity will not form. Accordingly, the stringency of the assay conditions determines the amount of complementarity needed between two nucleic acid strands to form a hybrid. Stringency is chosen to maximize the difference in stability between the hybrid formed with the target and other nucleic acid sequences.

The length of the target nucleic acid sequence and, accordingly, the length of the probe sequence can also be important. In some cases, there may be several sequences from a particular region, for example, a variable region varying in location and length, which yield probes with the desired hybridization characteristics. In other cases, one probe may be significantly better than another probe with a nucleotide sequence differing by a single base. While it is possible for nucleic acids that are not perfectly complementary to hybridize, the longest stretch of perfectly homologous base sequence will generally determine hybrid stability, with the composition of the base pairs also playing a role.

Regions of rRNA which form strong internal structures inhibitory to hybridization are less preferred target regions at least in assays in which helper probes are not used. Likewise, probe designs which result in extensive self complementarity should be avoided. If one of the two strands is wholly or partially involved in an intramolecular or intermolecular hybrid it will be less able to participate in the formation of a new intermolecular probe:target hybrid. Ribosomal RNA molecules are known to form very stable intramolecular helices and secondary structures by hydrogen bonding. By designing a hybridization assay so that a substantial portion of the targeted sequence remains in a single-stranded state until hybridization with the probe, the rate and extent of hybridization between probe and target may be greatly increased. One way this may be accomplished is by choosing as a target nucleotide sequence a sequence that is relatively uninvolved in intramolecular hydrogen-bonding. Alternatively or additionally, the hybridization assay probe may be used in a probe mix with helper oligonucleotides which can make the target site more accessible for hybridization with the hybridization assay probe.

A DNA target occurs naturally in a double-stranded form as does the product of the polymerase chain reaction (PCR). These double-stranded targets are naturally inhibitory to hybridization with a probe and require denaturation prior to hybridization. Appropriate denaturation and hybridization conditions are known in the art (e.g., E. M. Southern, *J. Mol. Bio.* 98:503 (1975)).

A number of formulae are available which will provide an estimate of the melting temperature for perfectly matched oligonucleotides to their target nucleic acids. One such formula, $$T_m=81.5+16.6(\log_{10}[Na^+])+0.41(\text{fraction } G+C)-(600/N)$$

(where N=the length of the oligonucleotide in number of nucleotides) provides a good estimate for the $T_m$ for oligonucleotides between 14 and 60 or 70 nucleotides in length. From such calculations, subsequent empirical verification or "fine tuning" of the $T_m$ may be made using screening techniques well known in the art. For further information on hybridization and oligonucleotide probes see, e.g., Sambrook et al., 2 Molecular Cloning: A Laboratory Manual (Cold Springs Harbor Laboratory Press 1989) hereby incorporated by reference herein (at Chapter 11). This reference, among others well known in the art, also provides estimates of the effect of mismatches on the $T_m$ of a hybrid. Thus, from the known nucleotide sequence of a given region of the ribosomal RNA (or rDNA) of two or more organisms, oligonucleotides may be designed which will distinguish these organisms from one another.

C. Nucleic Acid Amplification

Preferably, the amplification oligonucleotides of the present invention are oligodeoxynucleotides and are sufficiently long to be used as a substrate for the synthesis of extension products by a nucleic acid polymerase. Optimal primer length should take into account several factors, including the temperature of reaction, the structure and base composition of the primer, and how the primer is to be used. For example, for optimal specificity the oligonucleotide primer generally should contain at least about 12 nucleotides depending on the complexity of the target nucleic acid sequence. If such specificity is not essential, shorter primers may be used; in such a case, it may be desirable to carry out reaction at cooler temperatures in order to form stable hybrid complexes with the template nucleic acid.

Useful guidelines for designing amplification oligonucleotides and probes with desired characteristics are described herein. Our best mode target regions contain at least two and preferably three conserved regions of *Neisseria meningitidis* or *Neisseria gonorrhoeae* nucleic acid. These regions are about 15–350 in length; preferably 15–150 nucleotides in length.

The degree of amplification observed with a set of primers or promoter primers depends on several factors, including the ability of the oligonucleotides to hybridize to their complementary sequences and their ability to be extended or copied enzymatically. While oligonucleotides of different lengths and base composition may be used, oligonucleotides preferred in this invention have target binding regions of 18–40 bases with a predicted $T_m$ to target of about 65° C.

Parameters which affect hybridization of a probe such as $T_m$, complementarity and secondary structure of the target sequence also affect primer hybridization and therefore performance. The degree of non-specific extension (primer-dimer or non-target copying) can also affect amplification efficiency, therefore primers are selected to have low self- or cross-complementarity, particularly at the 3' ends of the sequence. Long homopolymer tracts and high GC content are avoided to reduce spurious primer extension. Computer programs are available to aid in this aspect of the design.

A nucleic acid polymerase used in conjunction with the amplification oligonucleotides of the present invention refers to a chemical, physical or biological agent which incorporates either ribo- or deoxyribonucleotides, or both, into a nucleic acid polymer, or strand, in a template-dependent manner. Examples of nucleic acid polymerases include DNA-directed DNA polymerases, RNA-directed DNA polymerases, and RNA-directed RNA polymerases. DNA polymerases bring about nucleic acid synthesis in a template-dependent manner and in a 5' to 3' direction. Because of the antiparallel orientation of the two strands in a double-stranded nucleic acid, this direction is from a 3' region on the template to a 5' region on the template. Examples of DNA-directed DNA polymerases include *E. coli* DNA polymerase I, the thermostable DNA polymerase from *Thermus aquaticus* (Taq), and the large fragment of DNA polymerase I from *Bacillus stearothermophilus* (Bst). Examples of RNA directed DNA polymerases include various retroviral reverse transcriptases, such as Moloney murine leukemia virus (MMLV) reverse transcriptase or avian myeloblastosis virus (AMV) reverse transcriptase.

During most nucleic acid amplification reactions, a nucleic acid polymerase adds nucleotide residues to the 3' end of the primer using the target nucleic acid as a template, thus synthesizing a second nucleic acid strand having a nucleotide sequence partially or completely complementary to a region of the target nucleic acid. In many nucleic acid amplification reactions, the two strands comprising the resulting double-stranded structure must be separated by chemical or physical means in order to allow the amplification reaction to proceed. Alternatively, the newly-synthesized template strand may be made available for hybridization with a second primer or promoter-primer by other means—e.g. through strand displacement or the use of a nucleolytic enzyme which digests part or all of the original target strand. In this way the process may be repeated through a number of cycles, resulting in a large increase in the number of nucleic acid molecules having the target nucleotide sequence.

Either the first or second amplification oligonucleotide, or both, may be a promoter-primer. Such a promoter-primer usually contains nucleotide sequences that are not complementary to those of the target nucleic acid molecule, or primer extension product(s). For example, Kacian and Fultz, U.S. Pat. No. 5,399,491 which is hereby incorporated by reference, describes various such oligonucleotides. These non-complementary sequences may be located 5' to the complementary sequences on the amplification oligonucleotide, and may provide a locus for initiation of RNA synthesis when made double-stranded through the action of a nucleic acid polymerase. The promoter thus provided may allow for the in vitro transcription of multiple RNA copies of the target nucleic acid sequence. It will be appreciated that when reference is made to a primer in this specification, such reference is intended to include the primer aspect of a promoter-primer as well unless the context of the reference clearly indicates otherwise.

In some amplification systems, for example the amplification method of Dattagupta et al., supra, the amplification oligonucleotides may contain 5' non-complementary nucleotides which assist in strand displacement. Furthermore, when used in conjunction with a nucleic acid polymerase having 5' exonuclease activity, the amplification oligonucleotides may have modifications at their 5' end to prevent enzymatic digestion. Alternatively, the nucleic acid polymerase may be modified to remove the 5' exonuclease activity, such as by treatment with a protease that generates an active polymerase fragment with no such nuclease activity. In such a case the oligonucleotides need not be modified at their 5' end.

1. Preparation of Oligonucleotides

All of the amplification oligonucleotides of the present invention can be readily prepared by methods known in the art. Preferably, the primers are synthesized using solid phase methods. For example, Caruthers, et al., describe using standard phosphoramidite solid phase chemistry to join nucleotides by phosphodiester linkages. Automated solid-phase chemical synthesis using cyanoethyl phosphoramidite precursors has been described by Barone, et al., *Nucleic Acids Research,* 12:405 (1984). (*Methods in Enzymology,* Volume 143, pg. 287 (1987)). Likewise, Bhatt describes a procedure for synthesizing oligonucleotides containing phosphorothioate linkages. (WO92/04358, entitled "Method and Reagent for Sulphurization of Organophosphorous Compounds", which enjoys common ownership with the present invention.) Also, Klem et al., entitled "Improved Process for the Synthesis of Oligomers", PCT WO 92/07864, describe the synthesis of oligonucleotides having different linkages including methylphosphonate linkages. The latter three references are hereby incorporated by reference herein. In addition, methods for the organic synthesis of oligonucleotides are known to those of skill in the art, and are described in Sambrook, et al., supra, previously incorporated by reference herein.

Following synthesis and purification of a particular oligonucleotide, several different procedures may be utilized to purify and control the quality of the oligonucleotide. Suitable procedures include polyacrylamide gel electrophoresis or high pressure liquid chromatography. Both of these procedures are well known to those skilled in the art.

All of the oligonucleotides of the present invention, whether hybridization assay probes, amplification oligonucleotides, or helper oligonucleotides, may be modified with chemical groups to enhance their performance or to facilitate the characterization of amplification products. For example, backbone-modified oligonucleotides such as those having phosphorothioate or methylphosphonate groups which render the oligonucleotides resistant to the nucleolytic activity of certain polymerases or to nuclease enzymes may allow the use of such enzymes in an amplification or other reaction. Another example of modification involves using non-nucleotide linkers (e.g., Arnold, et al., "Non-Nucleotide Linking Reagents for Nucleotide Probes", EP 0 313 219 hereby incorporated by reference herein) incorporated between nucleotides in the nucleic acid chain which do not interfere with hybridization or the elongation of the primer. Amplification oligonucleotides may also contain mixtures of the desired modified and natural nucleotides.

The 3' end of an amplification oligonucleotide may be blocked to prevent initiation of DNA synthesis as described by McDonough, et al., entitled "Nucleic Acid Sequence Amplification", WO94/03472 which enjoys common ownership with the present invention and is hereby incorporated by reference herein. A mixture of different 3' blocked amplification oligonucleotides, or of 3' blocked and unblocked oligonucleotides may increase the efficiency of nucleic acid amplification, as described therein.

As disclosed above, the 5' end of the oligonucleotides may be modified to be resistant to the 5'-exonuclease activity present in some nucleic acid polymerases. Such modifications can be carried out by adding a non-nucleotide group to the terminal 5' nucleotide of the primer using techniques such as those described by Arnold, et al., supra, entitled "Non-Nucleotide Linking Reagents for Nucleotide Probes", previously incorporated by reference herein.

Once synthesized, selected oligonucleotide probes may be labeled by any of several well known methods (e.g., J. Sambrook, supra). Useful labels include radioisotopes as well as non-radioactive reporting groups. Isotopic labels include $^{3}H$, $^{35}S$, $^{32}P$, $^{125}I$, $^{57}Co$ and $^{14}C$. Isotopic labels can be introduced into the oligonucleotide by techniques known in the art such as nick translation, end labeling, second strand synthesis, the use of reverse transcription, and by chemical methods. When using radiolabeled probes hybridization can be detected by autoradiography, scintillation counting, or gamma counting. The detection method selected will depend upon the particular radioisotope used for labeling.

Non-isotopic materials can also be used for labeling and may be introduced internally into the nucleic acid sequence or at the end of the nucleic acid sequence. Modified nucleotides may be incorporated enzymatically or chemically. Chemical modifications of the probe may be performed during or after synthesis of the probe, for example, through the use of non-nucleotide linker groups as described by Arnold, et al., supra "Non-Nucleotide Linking Reagents for Nucleotide Probes", previously incorporated by reference herein. Non-isotopic labels include fluorescent molecules, chemiluminescent molecules, enzymes, cofactors, enzyme substrates, haptens or other ligands.

Preferably, the probes are labeled with an acridinium ester. Acridinium ester labeling may be performed as described by Arnold et al., U.S. Pat. No. 5,185,439, entitled "Acridinium Ester Labeling and Purification of Nucleotide Probes" issued Feb. 9, 1993 and hereby incorporated by reference herein.

2. Amplification of Neisseria rRNA and rDNA

The amplification oligonucleotides of the present invention are directed to particular Neisseria 16S rRNA nucleotide sequences, or their rDNA counterparts. These amplification oligonucleotides may flank, overlap or be contained within at least one of the target nucleotide sequences used as a hybridization assay probe to detect the presence of Neisseria in a nucleic acid amplification assay. The amplification oligonucleotides described and claimed herein comprise two sets of amplification oligonucleotides. Members of the set of amplification oligonucleotides are able to hybridize with a nucleic acid having or substantially corresponding to one of the following nucleotide sequences:

SEQ ID NO: 23 GTCTTGAGAG GGAAAGCAGG GGAC

SEQ ID NO: 24 TATGTTACTC ACCCGTTCGC CACTCGCC

SEQ ID NO: 19 CTGAAGAATA AGCACCGGCT AACTACGTGC AGCAGC

SEQ ID NO: 21 CGATGACGGT ACCTGAAGAA TAAGCACCGG CTAAC

SEQ ID NO: 20 AACGGCCTTT TCTTCCCTGA CAAAAGTCCT TTACAACCCG

SEQ ID NO: 22 GTCCTTTACA ACCCGAAGGC CTTC

SEQ ID NO: 47 GUCUUGAGAG GGAAAGCAGG GGAC

SEQ ID NO: 48 UAUGUUACUC ACCCGUUCGC CACUCGCC

SEQ ID NO: 49 CUGAAGAAUA AGCACCGGCU AACUACGUGC AGCAGC

SEQ ID NO: 50 CGAUGACGGU ACCUGAAGAA UAAGCACCGG CUAAC

SEQ ID NO: 51 AACGGCCUU UCUUCCCUGA CAAAAGUCCU UUACAACCCG and

SEQ ID NO: 52 GUCCUUUACA ACCCGAAGGC CUUC

In preferred embodiments, these amplification oligonucleotides have or substantially correspond to the following sequences:

SEQ ID NO: 5 GTCCCCTGCT TTCCCTCTCA AGAC

SEQ ID NO: 6 GGCGAGTGGC GAACGGGTGA GTAACATA

SEQ ID NO: 7 GCTGCTGCAC GTAGTTAGCC GGTGCTTATT CTTCAG

SEQ ID NO: 8 GTTAGCCGGT GCTTATTCTT CAGGTACCGT CATCG

SEQ ID NO: 9 CGGGTTGTAA AGGACTTTTG TCAGGGAAGA AAAGGCCGTT

SEQ ID NO: 10 GAAGGCCTTC GGGTTGTAAA GGAC

SEQ ID NO: 41 GUCCCCUGCU UUCCCUCUCA AGAC

SEQ ID NO: 42 GGCGAGUGGC GAACGGGUGA GUAACAUA

SEQ ID NO: 43 GCUGCUGCAC GUAGUUAGCC GGUGCUUAUU CUUCAG

SEQ ID NO: 44 GUUAGCCGGU GCUUAUUCUU CAGGUACCGU CAUCG

SEQ ID NO: 45 CGGGUUGUAA AGGACUUUUG UCAGGGAAGA AAAGGCCGUU

SEQ ID NO: 46 GAAGGCCUUC GGGUUGUAAA GGAC

These oligonucleotides may also have additional, non-complementary bases at their 5' end comprising a promoter sequence able to bind an RNA polymerase and direct RNA transcription using the target nucleic acid as a template. For example the promoter, SEQ ID NO: 53 AATTTAATAC GACTCACTAT AGGGAGA may be used.

All of the amplification oligonucleotides of the present invention may have sequences which do not contain modifications or additions to these sequences. The amplification oligonucleotides may also or alternatively have modifications, such as blocked 3' and/or 5' termini or additions including but not limited to the addition of a specific nucleotide sequence that is recognized by an RNA polymerase, (e.g., the promoter sequence for T7, T3, or SP6 RNA polymerase), addition of sequences which enhance initiation or elongation of RNA transcription by an RNA polymerase, or sequences which may provide for intramolecular base pairing and encourage the formation of secondary or tertiary nucleic acid structures.

Amplification oligonucleotides are used in a nucleic acid amplification procedure, such as the polymerase chain reaction or an amplification reaction using RNA polymerase, DNA polymerase and RNAse H or its equivalent, as described by Kacian and Fultz supra, Dattagupta et al., supra, and by Sninsky et al., U.S. Pat. No. 5,079,351; all hereby incorporated by reference herein, the first two of which enjoy common ownership with the present invention.

A wide variety of methods are available to detect an amplified target sequence. For example, the nucleotide substrates or the primers can include a detectable label which is incorporated into newly synthesized DNA. The resulting labeled amplification product is then separated from the unused labeled nucleotides or primers and the label is detected in the separated product fraction.

Substances which can serve as useful detectable labels are well known in the art and include radioactive isotopes, fluorescent compounds, chemiluminescent compounds, chromophores, as well as ligands such as biotin and haptens which, while not directly detectable, can be readily detected by a reaction with labeled forms of their specific binding partners, e.g., avidin and antibodies, respectively.

Another approach is to detect the amplification product by hybridization with a detectably labeled nucleic acid probe and measuring the resulting hybrids in any conventional manner. In particular, the product can be assayed by hybridizing a chemiluminescent acridinium ester-labeled nucleic acid probe to the target sequence, selectively hydrolyzing the acridinium ester present on unhybridized probe, and measuring the chemiluminescence produced from the remaining acridinium ester in a luminometer. (see, e.g., Arnold, et al., supra, U.S. Pat. No. 5,283,174, and Nelson, et al., "Non-Isotopic DNA Probe Technologies", Academic Press, San Diego (Kricka, ed. 1992) both references hereby incorporated by reference herein.)

D. Oligonucleotide Hybridization Assay Probes to *Neisseria meningitidis* or *Neisseria gonorrhoeae* rRNA and rDNA The oligonucleotide hybridization assay probes disclosed and claimed herein are able to preferentially hybridize to target nucleic acids of *Neisseria meningitidis* rRNA or rDNA nucleotide sequences over nucleic acids of phylogenetically closely related bacterial species. These hybridization assay probes were designed, selected and/or chosen based upon a comparison of the nucleotide sequences of corresponding regions of the ribosomal RNA of *Neisseria meningitidis* and said phylogenetically closely-related species. In preferred embodiments these probes selectively hybridize to the nucleic acids of *Neisseria meningitidis* over the nucleic acids of *Neisseria gonorrhoeae.*

The present invention contemplates oligonucleotide hybridization probes that selectively hybridize to the nucleic acids of *Neisseria meningitidis* and not to the nucleic acids of *Neisseria gonorrhoeae* and include *Neisseria meningitidis* nucleic acid sequences having or substantially corresponding to the following nucleic acid sequences:

SEQ ID NO: 11 GGCTGTTGCT AATATCAGCG
SEQ ID NO: 12 GGCTGTTGCT AATACCAGCG
SEQ ID NO: 15 CGCTGATATT AGCAACAGCC
SEQ ID NO: 16 CGCTGGTATT AGCAACAGCC
SEQ ID NO: 25 GGCUGUUGCU AAUAUCAGCG
SEQ ID NO: 26 GGCUGUUGCU AAUACCAGCG
SEQ ID NO: 27 CGCUGAUAUU AGCAACAGCC
SEQ ID NO: 28 CGCUGGUAUU AGCAACAGCC

A number of oligonucleotide hybridization assay probes of the present invention preferably hybridize to target nucleic acids containing *Neisseria gonorrhoeae* rRNA or rDNA nucleotide sequences over nucleic acids of other phylogenetically closely related bacterial species. In preferred embodiments, these hybridization assay probes can distinguish *Neisseria gonorrhoeae* nucleic acids from *Neisseria meningitidis.*

The hybridization probes of the present invention that selectively hybridize to nucleic acids derived from *Neisseria gonorrhoeae* and not to the nucleic acids of *Neisseria meningitidis* have or substantially correspond to the following nucleotide sequences:

SEQ ID NO: 1 GAACGTACCG GGTAGCGG
SEQ ID NO: 3 GCCAATATCG GCGGCCGATG
SEQ ID NO: 29 CCGCTACCCG GTACGTTC
SEQ ID NO: 30 CATCGGCCGC CGATATTGGC
SEQ ID NO: 31 GAACGUACCG GGUAGCGG
SEQ ID NO: 32 GCCAAUAUCG GCGGCCGAUG
SEQ ID NO: 33 CCGCUACCCG GUACGUUC
SEQ ID NO: 34 CAUCGGCCGC CGAUAUUGGC

The oligonucleotide hybridization assay probes of the present invention are preferably labeled with a reporter group moiety such as a radioisotope, a fluorescent or chemiluminescent moiety, with an enzyme or other ligand, which can be used for detection or confirmation that the probe has hybridized to the target sequence. The Applicant most prefers the use of chemiluminescent acridinium esters as labels. See e.g. Arnold et al., U.S. Pat. No. 5,185,439, previously incorporated by reference herein. The assay probe is mixed with a sample suspected of containing a nucleic acid having the target sequence under hybridization conditions suitable for allowing annealing of the two strands by hydrogen bonding in the region of complementarity.

The probe may also be combined with one or more unlabeled helper oligonucleotides to facilitate binding to the nucleic acid having the target *Neisseria meningitidis* or *Neisseria gonorrhoeae* nucleotide sequence. The probe then hybridizes to the target nucleic acid present in the sample; the resulting hybrid duplex may be separated and detected by various techniques well known in the art, such as hydroxyapatite adsorption and radioactive monitoring. Also included among these techniques are those that involve selectively degrading the label present on unhybridized probe and then measuring the amount of label associated with the remaining hybridized probe, as disclosed in Arnold et al., U.S. Pat. No. 5,283,174, which enjoys common ownership with the present application and is incorporated by reference herein. This latter technique is presently preferred by the Applicants.

E. Helper Oligonucleotides Used in the Detection of Neisseria

Specific helper oligonucleotides were used to facilitate the hybridization of the hybridization assay probes to the target nucleic acid. Helper oligonucleotides are described in Hogan and Milliman, U.S. Pat. No. 5,030,557 entitled *Means and Method for Enhancing Nucleic Acid Hybridization,* which enjoys common ownership with the present application and is hereby incorporated by reference herein.

Helper probes are selected to hybridize to nucleic acid sequences located near the region targeted by the hybridization assay probe. Hybridization of the helper probe alters the secondary and tertiary structure of the target nucleic acid, facilitating the hybridization of the probe to the target nucleic acid.

Specific helper oligonucleotides for facilitating the specific detection of *Neisseria meningitidis* nucleic acids have or substantially correspond to one of these nucleotide sequences:

SEQ ID NO: 13 GCCTTCGGGT TGTAAAGGAC TTTTGTCAGG GAAGAAAA
SEQ ID NO: 14 GCTGATGACG GTACCTGAAG AATAAGCACC GGC
SEQ ID NO: 17 TTTTCTTCCC TGACAAAAGT CCTTTACAAC CCGAAGGC
SEQ ID NO: 18 GCCGGTGCTT ATTCTTCAGG TACCGTCATC AGC
SEQ ID NO: 35 GCCUUCGGGU UGUAAAGGAC UUUUGUCAGG GAAGAAAA
SEQ ID NO: 36 GCUGAUGACG GUACCUGAAG AAUAAGCACC GGC
SEQ ID NO: 37 UUUUCUUCCC UGACAAAAGU CCUUUACAAC CCGAAGGC
SEQ ID NO: 38 GCCGGUGCUU AUUCUUCAGG UACCGUCAUC AGC

In preferred embodiments, hybridization probes directed to *Neisseria meningitidis* nucleic acids substantially correspond to SEQ ID NOS: 11, 12, 25 or 26 used in a probe mixture together with a helper oligonucleotide having or substantially corresponding to the nucleotide sequence of:

SEQ ID NOS: 13, 14, 35 and 36

In other embodiments, a hybridization assay probe directed to *Neisseria meningitidis* nucleic acids substantially corresponding to SEQ ID NOS: 15, 16, 27 or 28 is used in a probe mixture together with a helper oligonucleotide having or substantially corresponding to a nucleotide sequence of:

SEQ ID NOS: 17, 18, 37 and 38

In a preferred embodiment, a hybridization probe directed to *Neisseria gonorrhoeae* ribosomal nucleic acid substantially corresponding to SEQ ID NOS: 1 or 31 is used in a mixture together with a helper oligonucleotide having or substantially corresponding to the nucleotide sequence of:

SEQ ID NOS: 2 or 39

In other preferred embodiments, a hybridization probe directed to *Neisseria gonorrhoeae* nucleic acids substantially corresponding to SEQ ID NOS: 3 or 32 is used in a probe mixture together with a helper oligonucleotide having or substantially corresponding to a nucleotide sequence of:

SEQ ID NOS: 4 or 40

Helper oligonucleotides generally may be used under stringent hybridization conditions, but are not necessarily species specific.

F. Nucleic Acid Compositions

In another related aspect, the invention features compositions comprising a nucleic acid hybrid between a hybridization assay probe and a nucleic acid sequence substantially complementary thereto (probe:target). One use of the hybrid formed between probe and target is to detect the presence of a target sequence. For example, acridinium ester ("AE") present in hybrids is resistant to hydrolysis in alkali solution whereas AE present in single-stranded nucleic acid is hydrolyzed in alkali solution (Arnold et al., entitled "Homogenous Protection Assay," EPO application number 88308767.8, publication number 309230, and by U.S. Pat. No. 5,238,174 hereby incorporated by reference). Thus, presence of target nucleic acids can be detected, after hydrolysis of the unbound AE-labeled probe, by measuring chemiluminescence of acridinium ester remaining associated with the nucleic acid hybrid.

The present invention also contemplates compositions comprising a nucleic acid hybrid between an amplification oligonucleotide and a nucleic acid sequence substantially complementary thereto (primer:target). One use the nucleic acid hybrid formed between primer and target is to provide an initiation site for a nucleic acid polymerase at the 3' end of the amplification oligonucleotide. For example, hybrids may form an initiation site for reverse transcriptase, DNA polymerases such as Taq polymerase or T4 DNA polymerase and RNA polymerases such as, T7 polymerase, SP6 polymerase, T3 polymerases and the like.

The present invention also features compositions comprising nucleic acid hybrids between a helper oligonucleotide and a nucleic acid sequence substantially complementary thereto (helper oligonucleotide:target). One use of the hybrid between the helper oligonucleotide and target is to make available a particular nucleic acid sequence for hybridization. For example, a hybrid between a helper oligonucleotide and its target may make a nucleic acid sequence capable of hybridizing to the target sequence available for hybridization with a hybridization probe. A full description of the use of helper oligonucleotides is provided in Hogan and Milliman, U.S. Pat. No. 5,030,557.

Compositions of the present invention include compositions for detecting *Neisseria meningitidis* nucleic acid comprising a nucleic acid hybrid formed between a nucleic acid derived from *Neisseria meningitidis* and an oligonucleotide having a nucleic acid sequence substantially corresponding to at least one of the nucleic acid sequences that follows:

SEQ ID NO: 11 GGCTGTTGCT AATATCAGCG
SEQ ID NO: 12 GGCTGTTGCT AATACCAGCG
SEQ ID NO: 15 CGCTGATATT AGCAACAGCC
SEQ ID NO: 16 CGCTGGTATT AGCAACAGCC
SEQ ID NO: 25 GGCUGUUGCU AAUAUCAGCG
SEQ ID NO: 26 GGCUGUUGCU AAUACCAGCG
SEQ ID NO: 27 CGCUGAUAUU AGCAACAGCC
SEQ ID NO: 28 CGCUGGUAUU AGCAACAGCC
SEQ ID NO: 13 GCCTTCGGGT TGTAAAGGAC TTTTGTCAGG GAAGAAAA
SEQ ID NO: 14 GCTGATGACG GTACCTGAAG AATAAGCACC GGC
SEQ ID NO: 17 TTTTCTTCCC TGACAAAAGT CCTTTACAAC CCGAAGGC

SEQ ID NO: 18 GCCGGTGCTT ATTCTTCAGG TACCGTCATC AGC
SEQ ID NO: 35 GCCUUCGGGU UGUAAAGGAC UUUUGUCAGG GAAGAAAA
SEQ ID NO: 36 GCUGAUGACG GUACCUGAAG AAUAAGCACC GGC
SEQ ID NO: 37 UUUUCUUCCC UGACAAAAGU CCUUUACAAC CCGAAGGC
SEQ ID NO: 38 GCCGGUGCUU AUUCUUCAGG UACCGUCAUC AGC
SEQ ID NO: 5 GTCCCCTGCT TTCCCTCTCA AGAC
SEQ ID NO: 6 GGCGAGTGGC GAACGGGTGA GTAACATA
SEQ ID NO: 7 GCTGCTGCAC GTAGTTAGCC GGTGCTTATT CTTCAG
SEQ ID NO: 8 GTTAGCCGGT GCTTATTCTT CAGGTACCGT CATCG
SEQ ID NO: 9 CGGGTTGTAA AGGACTTTTG TCAGGGAAGA AAAGGCCGTT
SEQ ID NO: 10 GAAGGCCTTC GGGTTGTAAA GGAC
SEQ ID NO: 41 GUCCCCUGCU UUCCCUCUCA AGAC
SEQ ID NO: 42 GGCGAGUGGC GAACGGGUGA GUAACAUA
SEQ ID NO: 43 GCUGCUGCAC GUAGUUAGCC GGUGCUUAUU CUUCAG
SEQ ID NO: 44 GUUAGCCGGU GCUUAUUCUU CAGGUACCGU CAUCG
SEQ ID NO: 45 CGGGUUGUAA AGGACUUUUG UCAGGGAAGA AAAGGCCGUU
SEQ ID NO: 46 GAAGGCCUUC GGGUUGUAAA GGAC

Preferred compositions of the present invention include compositions for detecting *Neisseria meningitidis* comprising a nucleic acid hybrid formed between a nucleic acid derived from *Neisseria meningitidis* and an oligonucleotide having a nucleic acid sequence substantially corresponding to at least one of the nucleic acid sequences that follows:

SEQ ID NO: 11 GGCTGTTGCT AATATCAGCG
SEQ ID NO: 12 GGCTGTTGCT AATACCAGCG
SEQ ID NO: 15 CGCTGATATT AGCAACAGCC
SEQ ID NO: 16 CGCTGGTATT AGCAACAGCC
SEQ ID NO: 25 GGCUGUUGCU AAUAUCAGCG
SEQ ID NO: 26 GGCUGUUGCU AAUACCAGCG
SEQ ID NO: 27 CGCUGAUAUU AGCAACAGCC
SEQ ID NO: 28 CGCUGGUAUU AGCAACAGCC

The present invention also contemplates compositions for detecting *Neisseria meningitidis* having a nucleic acid hybrid formed between a *Neisseria meningitidis*-derived nucleic acid and a hybridization assay probe having a nucleic acid sequence substantially corresponding to:

SEQ ID NO: 11 or SEQ ID NO: 25;

and which may also optionally contain a helper oligonucleotide hybridized to said nucleic acid which has a nucleic acid sequence which substantially corresponds to one of the following nucleic acid sequences:

SEQ ID NOS: 13, 14, 35 or 36.

The present invention also contemplates compositions for detecting *Neisseria meningitidis* having a nucleic acid hybrid formed between a *Neisseria meningitidis*-derived nucleic acid and a hybridization assay probe having a nucleic acid sequence substantially corresponding to:

SEQ ID NO: 12 or SEQ ID NO: 26;

and which may also optionally contain a helper oligonucleotide hybridized to said nucleic acid which has a nucleic acid sequence which substantially corresponds to one of the following nucleic acid sequences:

SEQ ID NOS: 13, 14, 35 or 36.

The present invention also contemplates compositions for detecting *Neisseria meningitidis* having a nucleic acid hybrid formed between a *Neisseria meningitidis*-derived nucleic acid and a hybridization assay probe having a nucleic acid sequence substantially corresponding to:

SEQ ID NO: 15 or SEQ ID NO: 27;

and which may also optionally contain a helper oligonucleotide hybridized to said nucleic acid which has a nucleic acid sequence which substantially corresponds to one of the following nucleic acid sequences:

SEQ ID NOS: 17, 18, 37 or 38.

The present invention also contemplates compositions for detecting *Neisseria meningitidis* having a nucleic acid hybrid formed between a *Neisseria meningitidis*-derived nucleic acid and a hybridization assay probe having a nucleic acid sequence substantially corresponding to:

SEQ ID NO: 16 or SEQ ID NO: 28;

and which may also optionally contain a helper oligonucleotide hybridized to said nucleic acid which has a nucleic acid sequence which substantially corresponds to one of the following nucleic acid sequences:

SEQ ID NOS: 17, 18, 37 or 38.

The present invention also contemplates compositions for detecting *Neisseria gonorrhoeae* having a nucleic acid hybrid formed between a *Neisseria gonorrhoeae*-derived nucleic acid and a hybridization assay probe having a nucleic acid sequence substantially corresponding to:

SEQ ID NO: 1 or SEQ ID NO: 31;

and which may also optionally contain a helper oligonucleotide hybridized to said nucleic acid which has a nucleic acid sequence which substantially corresponds to one of the following nucleic acid sequences:

SEQ ID NOS: 2 or 39.

The present invention also contemplates compositions for detecting *Neisseria gonorrhoeae* having a nucleic acid hybrid formed between a *Neisseria gonorrhoeae*-derived nucleic acid and a hybridization assay probe having a nucleic acid sequence substantially corresponding to:

SEQ ID NO: 3 or SEQ ID NO: 32;

and which may also optionally contain a helper oligonucleotide hybridized to said nucleic acid which has a nucleic acid sequence which substantially corresponds to one of the following nucleic acid sequences:

SEQ ID NOS: 4 or 40.

The present invention also contemplates compositions for detecting *Neisseria meningitidis* having a nucleic acid derived from *Neisseria meningitidis* and an oligonucleotide having a nucleic acid sequence substantially corresponding to SEQ ID NOS: 7 or 43 and/or an oligonucleotide having nucleic acid sequence substantially corresponding to at least one nucleic acid sequence that follows:

SEQ ID NOS: 9 or 45 and optionally has a hybridization assay probe capable of hybridizing to a *Neisseria meningitidis* nucleic acid and which has a nucleic acid sequence substantially corresponding to one of the following nucleic acid sequences:

SEQ ID NOS: 11, 15, 25 or 27 and which may also optionally contain a helper oligonucleotide which has a nucleic acid sequence which substantially corresponds to one of the following nucleic acid sequences:

SEQ ID NOS: 13, 14, 35 or 36.

The present invention also contemplates compositions for detecting *Neisseria meningitidis* having a nucleic acid derived from *Neisseria meningitidis* and an oligonucleotide with a nucleic acid sequence substantially corresponding to SEQ ID NOS: 7 or 43 and/or which also has an oligonucleotide having nucleic acid sequence substantially corresponding to at least one nucleic acid sequence that follows:

SEQ ID NOS: 9 or 45 and optionally has a hybridization assay probe capable of hybridizing to *Neisseria meningitidis* nucleic acids and which has a nucleic acid sequence substantially corresponding to one of the following nucleic acid sequences:

SEQ ID NOS: 12, 16, 26 or 28 and which may also optionally contain a helper oligonucleotide which has a nucleic acid sequence which substantially corresponds to one of the following nucleic acid sequences:

SEQ ID NOS: 13, 14, 35 or 36.

The present invention also contemplates compositions for detecting *Neisseria meningitidis* having a nucleic acid derived from *Neisseria meningitidis* and an oligonucleotide with a nucleic acid sequence substantially corresponding to SEQ ID NOS: 7 or 43 and/or which also has an oligonucleotide having nucleic acid sequence substantially corresponding to at least one nucleic acid sequence that follows:

SEQ ID NOS: 9 or 45 and optionally has a hybridization assay probe capable of hybridizing to a *Neisseria meningitidis* nucleic acid which has a nucleic acid sequence substantially corresponding to one of the following nucleic acid sequences:

SEQ ID NOS: 15, 11, 27 or 25 and which may also optionally contain a helper oligonucleotide which has a nucleic acid sequence which substantially corresponds to one of the following nucleic acid sequences:

SEQ ID NOS: 17, 18, 37 or 38.

The present invention also contemplates compositions for detecting *Neisseria meningitidis* having a nucleic acid derived from *Neisseria meningitidis* and an oligonucleotide with a nucleic acid sequence substantially corresponding to SEQ ID NOS: 7 or 43 and/or which also has an oligonucleotide having nucleic acid sequence substantially corresponding to at least one nucleic acid sequence that follows:

SEQ ID NOS: 9 or 45 and optionally has a hybridization assay probe capable of hybridizing to a *Neisseria meningitidis* nucleic acid which has a nucleic acid sequence substantially corresponding to one of the following nucleic acid sequences:

SEQ ID NOS: 16, 12, 28 or 20 and which may also optionally contain a helper oligonucleotide which has a nucleic acid sequence which substantially corresponds to one of the following nucleic acid sequences:

SEQ ID NOS: 17, 18, 37 or 38.

The present invention also contemplates compositions for detecting *Neisseria meningitidis* having a nucleic acid derived from *Neisseria meningitidis* and an oligonucleotide with a nucleic acid sequence substantially corresponding to SEQ ID NOS: 8 or 44 and/or which also has an oligonucleotide having nucleic acid sequence substantially corresponding to at least one nucleic acid sequence that follows:

SEQ ID NOS: 10 or 46 and optionally has a hybridization assay probe capable of hybridizing to a *Neisseria meningitidis* nucleic acid which has a nucleic acid sequence substantially corresponding to one of the following nucleic acid sequences:

SEQ ID NOS: 15, 11, 27 or 25 and which may also optionally contain a helper oligonucleotide which has a nucleic acid sequence which substantially corresponds to one of the following nucleic acid sequences:

SEQ ID NOS: 17, 18, 37 or 38.

The present invention also contemplates compositions for detecting *Neisseria meningitidis* having a nucleic acid derived from *Neisseria meningitidis* and an oligonucleotide with a nucleic acid sequence substantially corresponding to SEQ ID NOS: 8 or 44
and/or which also has an oligonucleotide having nucleic acid sequence substantially corresponding to at least one nucleic acid sequence that follows:
SEQ ID NOS: 10 or 46
and optionally has a hybridization assay probe capable of hybridizing to a *Neisseria meningitidis* nucleic acid which has a nucleic acid sequence substantially corresponding to one of the following nucleic acid sequences:
SEQ ID NOS: 16, 12, 28 or 26
and which may also optionally contain a helper oligonucleotide which has a nucleic acid sequence which substantially corresponds to one of the following nucleic acid sequences:
SEQ ID NOS: 17, 18, 37 or 38.

Preferred compositions of the present invention include compositions for detecting *Neisseria gonorrhoeae* comprising a nucleic acid hybrid formed between a nucleic acid derived from *Neisseria gonorrhoeae* and an oligonucleotide having a nucleic acid sequence substantially corresponding to at least one of the nucleic acid sequences that follow:
SEQ ID NO: 1 GAACGTACCG GGTAGCGG
SEQ ID NO: 3 GCCAATATCG GCGGCCGATG
SEQ ID NO: 29 CCGCTACCCG GTACGTTC
SEQ ID NO: 30 CATCGGCCGC CGATATTGGC
SEQ ID NO: 31 GAACGUACCG GGUAGCGG
SEQ ID NO: 32 GCCAAUAUCG GCGGCCGAUG
SEQ ID NO: 33 CCGCUACCCG GUACGUUC
SEQ ID NO: 34 CAUCGGCCGC CGAUAUUGGC
SEQ ID NO: 5 GTCCCCTGCT TTCCCTCTCA AGAC
SEQ ID NO: 6 GGCGAGTGGC GAACGGGTGA GTAACATA
SEQ ID NO: 7 GCTGCTGCAC GTAGTTAGCC GGTGCTTATT CTTCAG
SEQ ID NO: 8 GTTAGCCGGT GCTTATTCTT CAGGTACCGT CATCG
SEQ ID NO: 9 CGGGTTGTAA AGGACTTTTG TCAGGGAAGA AAAGGCCGTT
SEQ ID NO: 10 GAAGGCCTTC GGGTTGTAAA GGAC
SEQ ID NO: 41 GUCCCCUGCU UUCCCUCUCA AGAC
SEQ ID NO: 42 GGCGAGUGGC GAACGGGUGA GUAACAUA
SEQ ID NO: 43 GCUGCUGCAC GUAGUUAGCC GGUGCUUAUU CUUCAG
SEQ ID NO: 44 GUUAGCCGGU GCUUAUUCUU CAGGUACCGU CAUCG
SEQ ID NO: 45 CGGGUUGUAA AGGACUUUUG UCAGGGAAGA AAAGGCCGUU
SEQ ID NO: 46 GAAGGCCUUC GGGUUGUAAA GGAC
SEQ ID NO: 2 GGGATAACTG ATCGAAAGAT CAGCTAATAC CGCATACG
SEQ ID NO: 4 ACGGTACCTG AAGAATAAGC ACCGGCTAAC TACGTG
SEQ ID NO: 39 GGGAUAACUG AUCGAAAGAU CAGCUAAUAC CGCAUACG
SEQ ID NO: 40 ACGGUACCUG AAGAAUAAGC ACCGGCUAAC UACGUG More preferred compositions of the present invention include compositions for detecting *Neisseria gonorrhoeae* comprising a nucleic acid hybrid formed between a nucleic acid derived from *Neisseria gonorrhoeae* and an oligonucleotide having a nucleic acid sequence substantially corresponding to at least one of the nucleic acid sequences that follow:
SEQ ID NO: 1 GAACGTACCG GGTAGCGG
SEQ ID NO: 3 GCCAATATCG GCGGCCGATG
SEQ ID NO: 31 GAACGUACCG GGUAGCGG
SEQ ID NO: 32 GCCAAUAUCG GCGGCCGAUG
SEQ ID NO: 2 GGGATAACTG ATCGAAAGAT CAGCTAATAC CGCATACG
SEQ ID NO: 4 ACGGTACCTG AAGAATAAGC ACCGGCTAAC TACGTG
SEQ ID NO: 39 GGGAUAACUG AUCGAAAGAU CAGCUAAUAC CGCAUACG
SEQ ID NO: 40 ACGGUACCUG AAGAAUAAGC ACCGGCUAAC UACGUG The present invention also contemplates compositions for detecting *Neisseria gonorrhoeae* having a nucleic acid derived from *Neisseria gonorrhoeae* and an oligonucleotide with a nucleic acid sequence substantially corresponding to
SEQ ID NOS: 5 or 41
and/or which also optionally has an oligonucleotide having nucleic acid sequence substantially corresponding to at least one nucleic acid sequence that follows:
SEQ ID NOS: 6 or 42
and optionally has a hybridization assay probe capable of hybridizing to a *Neisseria gonorrhoeae* nucleic acid and which has a nucleic acid sequence substantially corresponding to one of the following nucleic acid sequences:
SEQ ID NOS: 1, 29, 31 or 33
and which may also optionally contain a helper oligonucleotide which as a nucleic acid sequence which substantially corresponds to one of the following nucleic acid sequences:
SEQ ID NOS: 2 or 39

The present invention also contemplates compositions for detecting *Neisseria gonorrhoeae* having a nucleic acid derived from *Neisseria gonorrhoeae* and an oligonucleotide with a nucleic acid sequence substantially corresponding to
SEQ ID NOS: 7 or 42
and/or which optionally has an oligonucleotide nucleic acid sequence substantially corresponding to at least one nucleic acid sequence that follows:
SEQ ID NOS: 9 or 45
and which optionally has a hybridization assay probe capable of hybridizing to a *Neisseria gonorrhoeae* nucleic acid and which has a nucleic acid sequence substantially corresponding to one of the following nucleic acid sequences:
SEQ ID NOS: 3, 30, 32 or 34
and which may also optionally contain a helper oligonucleotide which has a nucleic acid sequence which substantially corresponds to one of the following nucleic acid sequences:
SEQ ID NOS: 4 or 40
and which also optionally has an oligonucleotide having a nucleic acid sequence substantially corresponding to at least one nucleic acid sequence that follows:
SEQ ID NOS: 8 or 44

The present invention also contemplates compositions for detecting *Neisseria gonorrhoeae* having a nucleic acid derived from *Neisseria gonorrhoeae* and an oligonucleotide with a nucleic acid sequence substantially corresponding to
SEQ ID NOS: 10 or 46
and optionally has a hybridization assay probe capable of hybridizing to *Neisseria gonorrhoeae* nucleic acids and which has a nucleic acid sequence substantially corresponding to one of the following nucleic acid sequences:
SEQ ID NOS: 3, 30, 32 or 34
and/or which may also optionally contain a helper oligonucleotide which has a nucleic acid sequence which substantially corresponds to one of the following nucleic acid sequences:
SEQ ID NOS: 4 or 40

The present invention also contemplates nucleic acid hybrids comprising probes of the present invention and also at least one helper oligonucleotide that has a nucleic acid sequence substantially corresponding to at least one of the nucleic acid sequences that follows:

SEQ ID NO: 13 GCCTTCGGGT TGTAAAGGAC TTTTGTCAGG GAAGAAAA

SEQ ID NO: 14 GCTGATGACG GTACCTGAAG AATAAGCACC GGC

SEQ ID NO: 17 TTTTCTTCCC TGACAAAAGT CCTT-TACAAC CCGAAGGC

SEQ ID NO: 18 GCCGGTGCTT ATTCTTCAGG TAC-CGTCATC AGC

SEQ ID NO: 35 GCCUUCGGGU UGUAAAGGAC UUUUGUCAGG GAAGAAAA

SEQ ID NO: 36 GCUGAUGACG GUACCUGAAG AAUAAGCACC GGC

SEQ ID NO: 37 UUUUCUUCCC UGACAAAAGU CCU-UACAAC CCGAAGGC

SEQ ID NO: 38 GCCGGUGCUU AUUCUUCAGG UAC-CGUCAUC AGC

SEQ ID NO: 2 GGGATAACTG ATCGAAAGAT CAGCTAATAC CGCATACG

SEQ ID NO: 4 ACGGTACCTG AAGAATAAGC ACCG-GCTAAC TACGTG

SEQ ID NO: 39 GGGAUAACUG AUCGAAAGAU CAGCUAAUAC CGCAUACG

SEQ ID NO: 40 ACGGUACCUG AAGAAUAAGC ACCGGCUAAC UACGUG

The present invention also contemplates compositions for amplifying Neisseria nucleic acids comprising a nucleic acid hybrid formed between a Neisseria nucleic acid and an oligonucleotide having a nucleic acid sequence substantially corresponding to a nucleic acid sequence selected from the group consisting of:

SEQ ID NO: 5 GTCCCCTGCT TTCCCTCTCA AGAC

SEQ ID NO: 6 GGCGAGTGGC GAACGGGTGA GTAA-CATA

SEQ ID NO: 41 GUCCCCUGCU UUCCCUCUCA AGAC

SEQ ID NO: 7 GCTGCTGCAC GTAGTTAGCC GGT-GCTTATT CTTCAG

SEQ ID NO: 8 GTTAGCCGGT GCTTATTCTT CAGG-TACCGT CATCG

SEQ ID NO: 43 GCUGCUGCAC GUAGUUAGCC GGUGCUUAUU CUUCAG

SEQ ID NO: 44 GUUAGCCGGU GCUUAUUCUU CAG-GUACCGU CAUCG

SEQ ID NO: 9 CGGGTTGTAA AGGACTTTTG TCAGG-GAAGA AAAGGCCGTT

SEQ ID NO: 10 GAAGGCCTTC GGGTTGTAAA GGAC

SEQ ID NO: 45 CGGGUUGUAA AGGACUUUUG UCAGGGAAGA AAAGGCCGUU

SEQ ID NO: 46 GAAGGCCUUC GGGUUGUAAA GGAC

G. ASSAY METHODS

The present invention contemplates various methods for assaying for the presence of *Neisseria meningitidis* or *Neisseria gonorrhoeae* nucleic acid within a sample. One skilled in the art will understand that the exact assay conditions, probes or primers used will vary depending on the particular assay format used and the source of the sample.

Generally, the present invention contemplates methods for detecting the presence of *Neisseria meningitidis* by contacting a test sample under stringent hybridization conditions with a nucleic acid hybridization assay probe capable of preferentially hybridizing under stringent hybridization assay conditions to a *Neisseria meningitidis* target nucleic acid over nucleic acids from *Neisseria gonorrhoeae,* said target nucleic acid having a nucleic acid sequence substantially corresponding to a sequence selected from the group consisting of:

SEQ ID NO: 11 GGCTGTTGCT AATATCAGCG

SEQ ID NO: 12 GGCTGTTGCT AATACCAGCG

SEQ ID NO: 15 CGCTGATATT AGCAACAGCC

SEQ ID NO: 16 CGCTGGTATT AGCAACAGCC

SEQ ID NO: 25 GGCUGUGCU AAUAUCAGCG

SEQ ID NO: 26 GGCUGUGCU AAUACCAGCG

SEQ ID NO: 27 CGCUGAUAUU AGCAACAGCC

SEQ ID NO: 28 CGCUGGUAUU AGCAACAGCC

Preferred methods for detecting the presence of *Neisseria meningitidis* include the step of contacting a test sample under stringent hybridization conditions with a nucleic acid hybridization assay probe capable of preferentially hybridizing under stringent hybridization assay conditions to a *Neisseria meningitidis* target nucleic acid sequence over nucleic acid sequences of *Neisseria gonorrhoeae,* said target nucleic acid sequence substantially corresponding to a sequence selected from the group consisting of:

SEQ ID NO: 11 GGCTGTTGCT AATATCAGCG

SEQ ID NO: 12 GGCTGTTGCT AATACCAGCG

SEQ ID NO: 15 CGCTGATATT AGCAACAGCC

SEQ ID NO: 16 CGCTGGTATT AGCAACAGCC

Preferred methods for detecting the presence of *Neisseria gonorrhoeae* include the step of contacting a test sample under stringent hybridization conditions with a nucleic acid hybridization assay probe capable of preferentially hybridizing under stringent hybridization assay conditions to a *Neisseria gonorrhoeae* target nucleic acid sequence over a nucleic acid sequence of *Neisseria meningitidis*, said target nucleic acid sequence substantially corresponding to a sequence selected from the group consisting of:

SEQ ID NO: 1 GAACGTACCG GGTAGCGG

SEQ ID NO: 3 GCCAATATCG GCGGCCGATG

SEQ ID NO: 29 CCGCTACCCG GTACGTTC

SEQ ID NO: 30 CATCGGCCGC CGATATTGGC

SEQ ID NO: 31 GAACGUACCG GGUAGCGG

SEQ ID NO: 32 GCCAAUAUCG GCGGCCGAUG

SEQ ID NO: 33 CCGCUACCCG GUACGUUC

SEQ ID NO: 34 CAUCGGCCGC CGAUAUUGGC

In other embodiments, the present invention also contemplates methods for detecting the presence of *Neisseria gonorrhoeae* microorganisms by contacting a test sample under stringent hybridization conditions with a nucleic acid hybridization assay probe capable of preferentially hybridizing under stringent hybridization assay conditions to a *Neisseria gonorrhoeae* nucleic acid sequence over nucleic acid sequences from *Neisseria meningitidis*, said target nucleic acid sequences substantially corresponding to a sequence selected form the group consisting of:

SEQ ID NO: 1 GAACGTACCG GGTAGCGG

SEQ ID NO: 3 GCCAATATCG GCGGCCGATG

SEQ ID NO: 31 GAACGUACCG GGUAGCGG

SEQ ID NO: 32 GCCAAUAUCG GCGGCCGAUG

The present invention also contemplates methods of detecting Neisseria by first amplifying a portion of the Neisseria nucleic acid and then optionally using a hybridization assay probe of the present invention to assay for a specific Neisseria-derived nucleic acid amplified by the primers of the present invention. The amplified nucleic acid can be detected by a number of methods including gel electrophoresis.

In preferred embodiments, the present invention contemplates methods of detecting Neisseria-derived nucleic acid by first amplifying said nucleic acid with at least one amplification oligonucleotide that will bind to or cause elongation through one or more of the following sequences:

SEQ ID NO: 47 GUCUUGAGAG GGAAAGCAGG GGAC

SEQ ID NO: 48 UAUGUUACUC ACCCGUUCGC CACUCGCC
SEQ ID NO: 49 CUGAAGAAUA AGCACCGGCU AACUACGUGC AGCAGC
SEQ ID NO: 50 CGAUGACGGU ACCUGAAGAA UAAGCACCGG CUAAC
SEQ ID NO: 51 AACGGCCUUU UCUUCCCUGA CAAAAGUCCU UUACAACCCG
SEQ ID NO: 52 GUCCUUUACA ACCCGAAGGC CUUC
wherein said amplification oligonucleotide optionally has a nucleic acid sequence recognized by an RNA polymerase or which enhances initiation of elongation by an RNA polymerase.

This first method step is then optionally followed by detecting the amplified nucleic acid produced in the amplification step with an oligonucleotide hybridization assay probe able to specifically hybridize to nucleic acids derived from Neisseria species, *Neisseria cinerea, Neisseria meningitidis* or *Neisseria gonorrhoeae* under stringent hybridization conditions.

The amplification oligonucleotide used in the methods of the present invention may optionally have a nucleic acid sequence for example, a promoter sequence, recognized by an RNA polymerase or which enhances initiation by an RNA polymerase.

In other preferred embodiments, the present invention contemplates a method for amplifying Neisseria nucleic acids in a test sample by amplifying the nucleic acid with one or more amplification oligonucleotide that will bind to or cause elongation through a nucleic acid sequence substantially corresponding to the following nucleotide sequences:
SEQ ID NOS 19 or 49,
SEQ ID NOS 21 or 50, or
with a second amplification oligonucleotide that will bind to or cause elongation through a nucleic acid sequence substantially corresponding to one of the following sequences:
SEQ ID NOS: 20 or 51,
SEQ ID NOS: 22 or 52
or both, said amplification oligonucleotides, wherein at least one of said amplification oligonucleotides optionally has a nucleic acid sequence recognized by an RNA polymerase or which enhances initiation or elongation by an RNA polymerase.

In other more preferred embodiments, the present invention contemplates a method for amplifying Neisseria-derived nucleic acids in a test sample comprising amplifying said nucleic acid with one or more amplification oligonucleotide that will bind to or cause elongation through a nucleic acid sequence substantially corresponding to one of the following nucleotide sequences:
SEQ ID NOS: 19 or 49, or
with a second amplification oligonucleotide that will bind to or cause elongation through a nucleic acid sequence substantially corresponding to the following sequences:
SEQ ID NOS: 20 or 51,
or both said amplification oligonucleotides, wherein at least one of said amplification oligonucleotides optionally has a nucleic acid sequence recognized by an RNA polymerase or which enhances initiation or elongation by an RNA polymerase.

In other preferred embodiments, the present invention contemplates a method for increasing the number of Neisseria-derived nucleic acid sequences in a test sample comprising amplifying said nucleic acid with one or more amplification oligonucleotides that will bind to or cause elongation through a nucleic acid sequence substantially corresponding to the following nucleotide sequences:
SEQ ID NOS: 21 or 50,
or with a second amplification oligonucleotide that will bind to or cause elongation through a nucleic acid sequence substantially corresponding to the following sequences:
SEQ ID NOS: 22 or 52,
or both said amplification oligonucleotides, wherein at least one of said amplification oligonucleotides optionally has a nucleic acid sequence recognized by an RNA polymerase or which enhances initiation or elongation by an RNA polymerase.

The above methods may also include the further step of detecting the amplified nucleic acid with an oligonucleotide hybridization assay probe able to specifically hybridize to *Neisseria meningitidis* nucleic acids under stringent hybridization conditions.

Specifically, the methods may detect *Neisseria meningitidis* using oligonucleotide hybridization assay probes which will hybridize under stringent hybridization conditions to a nucleic acid sequence substantially corresponding to a sequence selected from the group consisting of:
SEQ ID NO: 11 GGCTGTTGCT AATATCAGCG
SEQ ID NO: 27 CGCUGAUAUU AGCAACAGCC
SEQ ID NO: 12 GGCTGTTGCT AATACCAGCG
SEQ ID NO: 28 CGCUGGUAUU AGCAACAGCC
SEQ ID NO: 15 CGCTGATATT AGCAACAGCC
SEQ ID NO: 25 GGCUGUUGCU AAUAUCAGCG
SEQ ID NO: 16 CGCTGGTATT AGCAACAGCC
SEQ ID NO: 26 GGCUGUUGCU AAUACCAGCG The present invention also contemplates methods for increasing the number of *Neisseria gonorrhoeae*-derived nucleic acids in a test sample by amplifying said nucleic acid with one or more amplification oligonucleotides that will bind to or cause elongation through a nucleic acid sequence substantially corresponding to one or more of the following nucleotide sequences:
SEQ ID NOs 23 or 47,
SEQ ID NOs 24 or 48,
and where the amplification oligonucleotide optionally has a nucleic acid sequence recognized by an RNA polymerase or which enhances initiation or elongation by an RNA polymerase.

Additional methods are contemplated for amplifying *Neisseria gonorrhoeae*-derived nucleic acids in a test sample with a first amplification oligonucleotide that will bind to or cause elongation through a nucleic acid sequence substantially corresponding to one of the following nucleotide sequences:
SEQ ID NOs: 23 or 47, or
with a second amplification oligonucleotide that will bind to or cause elongation through a nucleic acid sequence substantially corresponding to one of the following sequences:
SEQ ID NOs: 24 or 48, or
with both said first and second amplification oligonucleotides wherein one of the amplification oligonucleotides optionally has a nucleic acid sequence recognized by an RNA polymerase or which enhances initiation or elongation by an RNA polymerase.

These methods of amplifying a *Neisseria gonorrhoeae*-derived nucleic acid may be followed by the step of detecting the amplified nucleic acid with an oligonucleotide hybridization assay probe able to specifically hybridize to *Neisseria gonorrhoeae* nucleic acids under stringent hybridization conditions.

Preferably the oligonucleotide hybridization assay probe has a nucleic acid sequence substantially corresponding to a sequence selected from the group consisting of:
SEQ ID NOS: 1, 29, 31, and 33.

The detecting of *Neisseria gonorrhoeae* nucleic acid may include the use of a helper oligonucleotide having a nucleic acid sequence substantially corresponding to a nucleic acid sequence selected from the group consisting of:

SEQ ID NO: 2, and

SEQ ID NO: 39.

Other methods of detecting *Neisseria gonorrhoeae* nucleic acid are contemplated by increasing the number of *Neisseria gonorrhoeae*-derived nucleic acids in a test sample by amplifying said nucleic acid with one or more amplification oligonucleotide that will bind to or cause elongation through a nucleic acid sequence substantially corresponding to one or more of the following nucleotide sequences:

SEQ ID NOS: 19 or 49,

SEQ ID NOS: 20 or 51,

SEQ ID NOS: 21 or 50,

SEQ ID NOS: 22 or 52, and where the amplification oligonucleotide optionally has a nucleic acid sequence recognized by an RNA polymerase or which enhances initiation or elongation by an RNA polymerase.

Preferred methods for amplifying Neisseria nucleic acids in a test sample include amplifying the nucleic acid with one or more amplification oligonucleotide that will bind to or cause elongation through a nucleic acid sequence substantially corresponding to one of the following nucleotide sequences:

SEQ ID NOS: 19 or 49, or with a second amplification oligonucleotide that will bind to or cause elongation through a nucleic acid sequence substantially corresponding to one of the following sequences:

SEQ ID NOS: 20 or 51, or with both said first and second amplification oligonucleotides.

Alternatively the present invention contemplates amplifying Neisseria nucleic acids in a test sample comprising amplifying the nucleic acid with one or more amplification oligonucleotide that will bind to or cause elongation through a nucleic acid sequence substantially corresponding to one of the following nucleotide sequences:

SEQ ID NOS: 21 or 50, or with a second amplification oligonucleotides that will bind to or cause elongation through a nucleic acid sequence substantially corresponding to one of the following sequences:

SEQ ID NOS: 22 or 52, or with both said first and second amplification oligonucleotides.

The amplification of the Neisseria nucleic acid is preferably followed by detecting the amplified nucleic acid with an oligonucleotide hybridization assay probe able to specifically hybridize to *Neisseria gonorrhoeae* nucleic acids under stringent hybridization conditions. The oligonucleotide hybridization assay probe used preferably has a nucleic acid sequence substantially corresponding to a sequence selected from the group consisting of:

SEQ ID NOS: 3, 32, 30, 34

H. DIAGNOSTIC SYSTEMS

The present invention also contemplates diagnostic systems in kit form. A diagnostic system of the present invention may include a kit which contains, in an amount sufficient for at least one assay, amplification primers and/or hybridization assay probes of the present invention in a packaging material. Typically, the kits would also include instructions for use of the packaged primers and/or probes.

The various components of the diagnostic system may be provided in various forms. For example, the required enzymes, the nucleotide triphosphates, the primers and probes may be provided as a lyophilized reagent. These lyophilized reagents may be premixed before lyophilization so that when reconstituted form a complete mixture with the proper ratio of each of the components ready for use in the assay. In addition, the diagnostic systems of the present invention may contain a reconstitution reagent for reconstituting the lyophilized reagents of the kit. In preferred kits, the enzymes, nucleotides, triphosphates and required cofactors for the enzymes are provided as a single lyophilized reagent that when reconstituted forms a proper reagent for use in the present methods. In these preferred kits, a lyophilized primer agent may also be provided. In other preferred kits, lyophilized probe reagents are provided.

Typical packaging materials would include solid matrices such as glass, plastic, paper, foil, micro particles and the like, capable of holding within fixed limits hybridization assay probe or amplification primer of the present invention. Thus, for example, a package made from packaging materials can be a glass vial used to contain sub-milligram (i.e. picogram, nanogram etc.) quantities of a contemplated primer or hybridization assay probe or it could be a microtiter plate well to which the probes and/or primers of the present invention have been operatively affixed, i.e., linked so as to be capable of participating in a detection method of the present invention.

Instructions for use typically include a tangible expression describing the various reagents and/or concentrations of reagents and at least one assay method parameter which, for example, would be the relative amounts of reagents to use per amount of sample. In addition, such specifics as maintenance, time periods, temperature and buffer conditions may also be included.

The present invention contemplates diagnostic systems or kits containing the oligonucleotides of a composition of the present invention. The present invention also contemplates diagnostic systems or kits containing the oligonucleotides required to perform a method of the present invention.

This method preferably also uses a helper oligonucleotide having a nucleic acid sequence substantially corresponding to a nucleic acid sequence selected from the group consisting of:

SEQ ID NO. 4: and

SEQ ID NO. 40:

The present invention contemplates diagnostic systems or a kit containing at least one oligonucleotide having a nucleic acid sequence substantially corresponding to a nucleic acid sequence selected from the group consisting of:

SEQ ID NOS: 1, 3, 11, 12, 15, 16, 29, 30, 33, 34, 27, 28, 25, 26.

The present invention contemplates diagnostic systems or a kit having an oligonucleotide hybridization assay probe having at least one helper probe having a nucleic acid sequence substantially corresponding to the sequence selected from the group consisting of:

SEQ ID NOS: 2 or 39, when said oligonucleotide substantially corresponds to

SEQ ID NOS: 1 or 31;

or

SEQ ID NOS: 4 or 40, when said oligonucleotide substantially corresponds to

SEQ ID NOS: 3 or 32;

or

SEQ ID NOS: 13 or 35, or

SEQ ID NOS: 14 or 36, when said oligonucleotide substantially corresponds to

SEQ ID NOS: 11 or 25, or

SEQ ID NOS: 12 or 26;
or
SEQ ID NOS: 17 or 37,
SEQ ID NOS: 18 or 38,
when said oligonucleotide substantially corresponds to
SEQ ID NOS: 15 or 27, or
SEQ ID NOS: 16 or 28.

The present invention contemplates diagnostic systems or a kit containing two oligonucleotides having a nucleic acid sequence substantially corresponding to a nucleic acid sequence selected from the group consisting of:

SEQ ID NO: 7 GCTGCTGCAC GTAGTTAGCC GGTGCTTATT CTTCAG
SEQ ID NO: 8 GTTAGCCGGT GCTTATTCTT CAGGTACCGT CATCG
SEQ ID NO: 9 CGGGTTGTAA AGGACTTTTG TCAGGGAAGA AAAGGCCGTT
SEQ ID NO: 10 GAAGGCCTTC GGGTTGTAAA GGAC
SEQ ID NO: 43 GCUGCUGCAC GUAGUUAGCC GGUGCUUAUU CUUCAG
SEQ ID NO: 44 GUUAGCCGGU GCUUAUUCUU CAGGUACCGU CAUCG
SEQ ID NO: 45 CGGGUUGUAA AGGACUUUUG UCAGGGAAGA AAAGGCCGUU
SEQ ID NO: 46 GAAGGCCUUC GGGUUGUAAA GGAC optionally having a 5' sequence recognized by an RNA polymerase or which enhances initiation or elongation by an RNA polymerase.

The present invention contemplates diagnostic systems or a kit containing oligonucleotides having a nucleic acid sequence substantially corresponding to the following sequences:

SEQ ID NOS: 7 or 43,
SEQ ID NOS: 9 or 45,
SEQ ID NOS: 11 or 25,
SEQ ID NOS: 13 or 35,
SEQ ID NOS: 14 or 36.

The present invention contemplates diagnostic systems or a kit containing oligonucleotides having a nucleic acid sequence substantially corresponding to the following sequences:

SEQ ID NOS: 15 or 27,
SEQ ID NOS: 16 or 26,
SEQ ID NOS: 17 or 37,
SEQ ID NOS: 18 or 38.

The present invention contemplates diagnostic systems or a kit containing oligonucleotides having a nucleic acid sequence substantially corresponding to the following sequences:

SEQ ID NOS: 7 or 43,
SEQ ID NOS: 9 or 45,
SEQ ID NOS: 15 or 27,
SEQ ID NOS: 16 or 28,
SEQ ID NOS: 17 or 37,
SEQ ID NOS: 18 or 38.

The present invention contemplates diagnostic systems or a kit containing oligonucleotides having a nucleic acid sequence substantially corresponding to the following sequences:

SEQ ID NOS: 5 or 41,
SEQ ID NOS: 6 or 42,
SEQ ID NOS: 2 or 39,
SEQ ID NOS: 1 or 31.

The present invention contemplates diagnostic systems or a kit containing oligonucleotides having a nucleic acid sequence substantially corresponding to the following sequences:

SEQ ID NOS: 5 or 41,
SEQ ID NOS: 2 or 39,
SEQ ID NOS: 1 or 31.

EXAMPLES

Examples are provided below to illustrate different aspects and embodiments of the present invention. These examples are not intended in any way to limit the disclosed invention, which is limited only by the claims.

Probes specific for *Neisseria meningitidis* were designed using sequences determined in prospective target areas using primers complementary to the 16S rRNAs of *Neisseria gonorrhoeae* (ATCC NO. 19424), *Neisseria meningitidis* sero group A (ATCC NOs 13077), serogroup C (ATCC No. 23248) and serogroup L (ATCC No. 43828), and clinical isolates, *Neisseria lactamica* (ATCC NO. 23970), *Neisseria cinerea* (ATCC NO. 14685), *Neisseria mucosa* (ATCC NO. 19696), *Neisseria sicca* (ATCC NO. 29193) and *Kingella kingae* (ATCC NO. 23330). The nucleic acid sequence from phylogenetically near neighbors, including the published sequence of *Neisseria gonorrhoeae* NCTC 8375 Rossau et al., Nuc. Acids Res. 16:6227 were also used as comparisons with the nucleic sequence from *Neisseria meningitidis* to determine variable regions.

An example of such an alignment follows: A specific sequence in which *Neisseria meningitidis* varied from *E. coli* and *Neisseria gonorrohoeae* was chosen for probe design. Two different probes were designed to *Neisseria meningitidis* (SEQ ID NO: 11) and (SEQ ID NO: 12). The rRNA sequences are shown below:

```
E. coli          GAGUAAAG(UUAAUAC)CUUUG  SEQ ID NO: 54
                 .      .   .. .. .   .
                 GGCTGTTG(CTAATAC)CAGCG  SEQ ID NO: 12
                 ........ ......  .....
                 GGCTGTTG(CTAATAT)CAGCG  SEQ ID NO: 11
                 ... .  . . .. .  .....
N. meningiti-    GGCUGUUG(CUAAUAU)CAGCG  SEQ ID NO: 55
dis.c
                 ........ . ..... . . .
N. gonorrho-     GGCUGUUG(CCAAUAU)CGGGG  SEQ ID NO: 56
eae.P
```

The following hybridization assay probe sequences are featured in the examples described below:

SEQ ID NO: 1 GAACGTACCG GGTAGCGG,
SEQ ID NO: 3 GCCAATATCG GCGGCCGATG,
SEQ ID NO: 11 GGCTGTTGCTAATATCAGCG,
SEQ ID NO: 12 GGCTGTTGCTAATACCAGCG,
SEQ ID NO: 15 CGCTGATATTAGCAACAGCC, and
SEQ ID NO: 16 CGCTGGTATTAGCAACAGCC

Example 1

In this experiment, purified *N. gonorrhoeae* rRNA (ATCC NO. 19424) was amplified with oligonucleotides containing sequences complementary to *N. gonorrhoeae* rRNA using the techniques described in Kacian et al. U.S. Pat. No. 5,399,491. Two promoter primers were synthesized, each containing a T7 RNA polymerase promoter sequence 5'-AATTTAATACGACTCACTATAGGGAGA-3' SEQ ID NO. 53 at the 5' end, covalently attached to a target complementary sequence 5'-GTCCCCTGCTTTCCCTCTCAAGAC-3' (SEQ ID NO. 5) at the 3' end. One promoter primer was synthesized with a free 3' OH group, and was used at two pmol per reaction. The second promoter primer was synthesized with an alkane diol group at the 3' end and was used at 13 pmol per reaction. The target nucleic acid and primers were heated to 95° C. for 15 minutes and cooled to 42° C. Moloney Murine Leukemia Virus reverse transcriptase (MMLV RT), 900 units, and 400 units of T7 RNA polymerase were added. The final amplification mixture contained 50 mM Tris HCl (pH 8.5), 35 mM potassium chloride, 4 mM GTP, 4 mM ATP, 4 mM DTP, 4 mM CTP, 1 mM dATP, 1 mM dTTP, 1 mM dCTP, 1 mM dGTP, 20 mM MgCl2, 20 mM N-Acetyl-L-Cysteine, and 5% (w/v) glycerol. After a two hour incubation at 42° C., the entire one hundred μl amplification reaction was assayed by hybridization with an acridinium ester labeled probe of sequence 5'-GAACGTACCGGGTAGCGG-3' (SEQ. ID. NO. 1) and an unlabeled helper probe of sequence 5'-GGGATAACTGATCGAAAGATCAGCTAATACCGCA TACG-3' (SEQ. ID. NO. 2) Hybridization was performed in 200 μl of a solution containing 0.05 M lithium succinate (pH 5), 0.6 M LiCl, 1% (w/v) lithium lauryl sulfate, 10 mM EDTA, 10 mM EGTA, at 60° C. for 10 minutes, followed by addition of 300 μl of 0.15 M sodium tetraborate pH 8.5, 1% TRITON® X-100. This mixture was incubated at 60° C. for 10 minutes, and cooled to room temperature. The remaining chemiluminescence in each tube was assayed in a Gen-Probe LEADER® I luminometer equipped with automatic injection of 1 mM nitric acid and 0.1% (v/v) hydrogen peroxide followed by injection of a solution containing 1 N sodium hydroxide. Results were given in Relative Light Units (RLU), a measure of the photons detected by the luminometer.

TABLE 1

Amplification of *Neisseria gonorrhoeae* nucleic acid with amplification oligonucleotides comprising SEQ ID NO. 5 followed by detection with a probe comprising SEQ ID NO. 1.

| Amount of target | RLU |
|---|---|
| 0.1 pg* | 103,596 |
| | 99,931 |
| | 123,512 |
| 0.025 pg | 25,636 |
| | 39,454 |
| | 29,594 |
| 0 pg | 1,084 |
| | 1,012 |
| | 640 |

*pg = picogram

Example 2

This experiment demonstrates amplification of *N. gonorrhoeae* rRNA with two primers of opposite sense. The promoter-primer described in Example 1 containing a T7 RNA polymerase promoter sequence and a 3' target hybridizing region of sequence 5'-GTCCCCTGCTTTCCCTCTCAAGAC-3' (SEQ. ID. NO. 5) was used at 15 pmol per reaction and a primer containing a sequence of the same sense as *N. gonorrhoeae* rRNA, 5'-GGCGAGTGGCGAACGGGTGAGTAACATA-3' (SEQ. ID. NO. 6) was used at 15 pmol per reaction. Reactions were performed in triplicate. The amplification conditions were as described in Example 1, and samples were heated to 95° C. for 5 minutes, then cooled to 42° C. Enzymes were added, and after a two hour incubation at 42° C., 20 μl of the amplification reaction was assayed by hybridization with an acridinium ester labeled probe synthesized with sequence SEQ. ID. NO. 1 and an unlabeled helper probe synthesized with sequence SEQ. ID. NO. 2. The primers amplified *N. gonorrhoeae* RNA and allowed detection of less than 100 copies of target.

TABLE 2

Amplification of *N. gonorrhoeae* rRNA with primers comprising SEQ. ID. NOs. 5 and 6 and detection with a probe comprising SEQ ID NO. 1.

| Amount of rRNA target added | RLU |
|---|---|
| 500 copies (0.0012 pg) | 334,838 |
| | 343,107 |
| | 1,320,194 |
| 80 copies (0.0002 pg) | 255,898 |
| | 1,512,486 |
| | 377,938 |
| 0 pg | 2,354 |
| | 2,454 |
| | 2,440 |

Example 3

In this experiment, two promoter primers of identical sequence were again used. Each promoter primer was synthesized with a 5' T7 RNA polymerase promoter sequence 5'-AATTTAATACGACTCACTATAGGGAGA-3' (SEQ ID NO: 53) at the 5' end and a target hybridizing region 5'-GCTGCTGCACGTAGTTAGCCGGTGGTTATTCTTCA G-3' (SEQ ID NO. 7) at the 3' end. The promoter primers were synthesized either with a 3'-hydroxyl group and used at 2 pmol per reaction, or with a 3'-alkane diol and used at 13 pmol per reaction. Samples were heated to 95° C. for 5 minutes and cooled to 42° C. prior to enzyme addition. The amplification conditions were as described in Example 1. After a two hour incubation at 42° C., 100 μl of the amplification reaction was assayed by hybridization with an acridinium ester labeled probe synthesized with sequence 5'-GCCAATATCGGCGGCCGATG-3' (SEQ. ID. NO. 3) and an unlabeled helper probe with the sequence 5'-ACGGTACCTGAAGAATAAGCACCGGCTAACTACG TG-3' (SEQ. ID. NO. 4) using the conditions described in Example 1.

TABLE 3

Amplification of *N. gonorrhoeae* rRNA using primers comprising SEQ ID NO. 7.

| Amount of rRNA target added | RLU with probe SEQ ID NO. 3 |
|---|---|
| 0.025 pg | 95,905 |
| | 49,717 |
| | 59,774 |
| 0.0125 pg | 10,520 |
| | 12,576 |
| | 12,322 |
| 0.005 pg | 19,498 |
| | 40,962 |
| | 21,722 |
| 0 pg | 2,888 |
| | 2,792 |
| | 2,777 |

Example 4

In this experiment, *N. gonorrhoeae* rRNA was amplified with a mixture of two oligonucleotides, one a promoter primer complementary to *N. gonorrhoeae* rRNA and one primer of the same sense as *N. gonorrhoeae* rRNA. The promoter primer contained a T7 RNA polymerase promoter sequence at the 5' end and a target hybridizing region 5'-GCTGCTGCACGTAGTTAGCCGGTGCTTATTCTTCAG-3' (SEQ ID NO. 7) at the 3' end and was used with a primer of sequence 5'-CGGGTTGTAAAGGACTTTTGTCAGGGAAGAAAAGGCCGTT-3' (SEQ. ID. NO. 9) at 30 pmol per reaction. Alternatively, a promoter primer containing a target hybridizing region of sequence 5'-GTTAGCCGGTGCTTATTCTTCAGGTACCGTCATCG-3' (SEQ. ID. NO. 8) was used at 15 pmol per reaction with the promoter primer with a sequence 5'-GAAGGCCTTCGGGTTGTAAAGGAC-3' (SEQ. ID. NO. 10), at 15 pmol per reaction. Amplification conditions were as described for Example 1. Twenty μl of the product was assayed by hybridization with an acridinium ester labeled probe synthesized with sequence 5'-GCCAATATCGGCGGCCGATG-3' (SEQ. ID. NO. 3) and an unlabeled helper probe synthesized with the sequence 5'-ACGGTACCTGAAGAATAAGCACCGGCTAACTACGTG-3' (SEQ. ID. NO. 4) as described in Example 1.

TABLE 4

Amplification of *N. gonorrhoeae* rRNA using primers comprising SEQ ID NOs. 7 and 9 or 8 and 10.

| | RLU with probe SEQ ID NO. 3 | |
|---|---|---|
| Amount of rRNA target added Primer sequences: | SEQ ID NOS. 7 and 9 | SEQ ID NOS. 8 and 10 |
| 0.5 pg | 817,344 | 680,836 |
| | 802,901 | 603,811 |
| | 785,206 | 619,969 |
| 0.05 pg | 188,661 | 132,359 |
| | 192,656 | 157,509 |
| | 204,878 | 87,161 |
| 0.005 pg | 25,276 | 51,398 |
| | 26,451 | 40,032 |
| | 24,915 | 55,968 |
| 0 pg | 3,600 | 2,189 |
| | 3,366 | 2,205 |
| | 888 | |

Example 5

This example demonstrates the reactivity of the amplification and detection assay. Fresh cultures of thirteen strains of *N. gonorrhoeae* were suspended in 0.9% sodium chloride at a density of approximately $10^{10}$ cells/ml and lysed in a solution containing 3% (w/v) lithium lauryl sulfate, 30 mM sodium phosphate pH 6.8, 1 mM EDTA and 1 mM EGTA. Release of nucleic acid was confirmed by hybridization with a probe directed to a conserved region of ribosomal RNA of all bacteria. The cell lysates were further diluted in water and added to amplification reactions containing 30 pmol of a promoter-primer containing a 5' T7 RNA promoter sequence SEQ ID NO: 53 5'-AATTTAATACGACTCACTATAGGGAGA-3' and a 3' target binding sequence comprising SEQ. ID. NO. 7, and 30 pmol of primer comprising sequence SEQ. ID. NO. 9. Duplicate reactions containing lysate from at least $10^5$ cells were performed using an amplification mixture containing 50 mM Tris HCl (pH 8.5), 35 mM potassium chloride, 4 mM GTP, 4 mM ATP, 4 mM UTP, 4 mM CTP, 1 mM dATP, 1 mM dTTP, 1 mM dCTP, 1 mM dGTP, 20 mM MgCl2, 20 mM N-acetyl-L-cysteine, 5% (v/v) glycerol and the oligonucleotide primers described above. The mixture was heated to 95° C. for 5 minutes, cooled to 42° C. and 900 units of MMLV reverse transcriptase and 400 units of T7 RNA polymerase were added. After a one hour incubation at 42° C., 20 μl of amplification reaction was assayed by hybridization with an acridinium ester labeled probe synthesized with sequence 5'GCCAATATCGGCGGCCGATG-3' (SEQ. ID. NO. 3) and an unlabeled helper probe containing sequence 5'-ACGGTACCTGAAGAATAAGCACCGGCTAACTACGTG-3' (SEQ. ID. NO. 4).

TABLE 5

Amplification of different strains of *N. gonorrhoeae* using primers comprising SEQ ID NOs. 7 and 9.

| *N. gonorrhoeae* ATCC. No. | RLU with probe SEQ ID NO. 3 |
|---|---|
| 9793 | 1,150,477 |
| | 1,162,284 |
| 9826 | 1,173,586 |
| | 1,149,251 |
| 9827 | 1,093,440 |
| | 1,080,405 |
| 9828 | 1,143,960 |
| | 1,149,465 |
| 9830 | 1,165,108 |
| | 1,143,063 |
| 10150 | 1,105,754 |
| | 1,131,598 |
| 10874 | 1,139,487 |
| | 1,103,912 |
| 11688 | 1,024,195 |
| | 1,112,160 |
| 11689 | 1,141,404 |
| | 1,116,069 |
| 19424 | 1,104,256 |
| | 1,116,832 |
| 27628 | 1,133,696 |
| | 1,117,624 |
| 27630 | 1,132,496 |
| | 1,146,161 |
| 27631 | 1,089,105 |
| | 1,070,058 |

Example 6

Sequence analysis of other Neisseria species indicated that the amplification oligonucleotides of this invention could amplify nucleic acids of other species. This example demonstrates the utility of the amplification oligonucleotides of this invention to amplify nucleic acid from another Neisseria species, *N. meningitidis.* In the course of development of a specific probe for *N. meningitidis,* it became clear that the members of the species *N. meningitidis* were not homogeneous in the probe region of choice. The sequences of 16S rRNAs of representative *N. meningitidis* species which showed low reactivity to the initial probe were determined and a second probe was designed. These data demonstrate the differential reactivity of three *N. meningitidis* species to the two probes. In this example, purified RNA from *Neisseria gonorrhoeae* (ATCC No. 19424), or lysates from *Neisseria meningitidis* serogroup A (ATCC No. 13077), serogroup C (ATCC No. 13102) and serogroup L, (ATCC No. 43828) representing approximately 1,000 cells were amplified with a promoter-primer and primer described in Example 5 under the conditions described in Example 5. Ten μl samples of the 100 μl amplification reactions were assayed by hybridization with an acridinium ester labeled probe synthesized with sequence 5'-GCCAATATCGGCGGCCGATG-3' (SEQ ID NO. 3) and an unlabeled helper probe synthesized with the sequence 5'-ACGGTACCTGAAGAATAAGCACCGGCTAACTACGTG-3, (SEQ ID NO. 4), or an acridinium ester labeled probe synthesized with the sequence 5'-GGCTGTTGCTAATATCAGCG-3' (SEQ ID NO. 11) and two unlabeled helper probes, one synthesized with sequence 5'-GCCTTCGGGTTGTAAAGGACTTTTGTCAGGGAAGAAAA-3' (SEQ ID NO. 13) and one synthesized with the sequence 5'-GCTGATGACGGTACCTGAAGAATAAGCACCGGC-3'(SEQ ID NO. 14), or an acridinium ester labeled probe synthesized with sequence 5'-GGCTGTTGCTAATACCAGCG-3'(SEQ ID NO. 12) with unlabeled helper probes SEQ ID NO: 13 and 14 or with a combination of labeled probes SEQ ID NO: 11 and 12 used with unlabeled helper probes SEQ ID NO: 13 and 14. Sequence analysis indicated that other strains of Neisseria will also amplify with these primers.

TABLE 6

Amplification of *Neisseria gonorrhoeae* and *Neisseria meningitidis* strains using primers comprising SEQ ID NOs. 7 and 9.

| | RLU Probe SEQ ID NOs: | | | |
|---|---|---|---|---|
| | 3 | 11 | 12 | 11 + 12 |
| | Helper probe SEQ ID NOs: | | | |
| Organism | 4 | 13 + 14 | 13 + 14 | 13 + 14 |
| *N. gonorrhoeae* | 1,017,626 | 1,660 | 820 | 1,603 |
| | 994,788 | 1,448 | 809 | 1,559 |
| | 1,030,242 | 1,743 | 805 | 1,792 |
| *N. meningitidis* | 2,059 | 1,208,967 | 3,534 | 829,251 |
| Serogroup A | 1,861 | 1,115,956 | 3,700 | 760,360 |
| | 2,183 | 1,138,675 | 3,546 | 775,675 |
| *N. meningitidis* | 1,931 | 1,164,254 | 2,819 | 749,502 |
| Serogroup C | 2,130 | 1,068,489 | 2,477 | 687,517 |
| | 1,963 | 1,110,933 | 3,103 | 803,732 |
| *N. meningitidis* | 1,833 | 85,321 | 1,206,045 | 1,537,314 |
| Serogroup L | 1,972 | 79,555 | 1,199,815 | 1,474,016 |
| | 1,814 | 77,797 | 1,211,022 | 1,645,742 |

The data show that strains of *N. meningitidis* and *N. gonorrhoeae* can be amplified using primers comprising SEQ ID NOs. 7 and 9 and detected with probes of SEQ ID NOs. 3, 11, and 12.

Example 7

The sensitivity of the amplification and detection assay for *N. meningitidis* were demonstrated in this experiment. In this example, *Neisseria meningitidis* serogroup C cells were cultured and suspended in 0.9% sodium chloride to a density of approximately $10^9$ cells per ml. Cells were lysed following addition of an equal volume of a solution containing 3% (w/v) lithium lauryl sulfate, 30 mM sodium phosphate (pH 6.8), 1 mM EDTA, 1 mM EGTA and diluted with water prior to addition to the amplification reactions. Amplifications were performed as described for Example 5 using the promoter primer and primer described in Example 5 (SEQ ID NOs. 7 and 9, respectively). Twenty $\mu$l of the reaction was analyzed by hybridization in the HPA format using an acridinium ester labeled probe synthesized with the sequence 5'-GGCTGTTGCTAATATCAGCG-3' (SEQ ID NO. 11) and two unlabeled helper probes, one synthesized with the sequence 5'-GCCTTCGGGTTGTAAAGGACTTTTGTCAGGGAAGAAAA-3' (SEQ ID NO. 13) and one synthesized with the sequence 5'-GCTGATGACGGTACCTGAAGAATAAGCACCGGC-3' (SEQ ID NO. 14).

TABLE 7

Amplification of *N. meningitidis* serogroup A with amplification oligomers comprising SEQ ID NOs. 7 and 9, followed by detection with probe SEQ ID NO. 11.

| Amount of target added | RLU with probe SEQ ID NO. 11 |
|---|---|
| 40 cells | 723,645 |
| | 648,069 |
| | 686,492 |
| 4 cells | 195,370 |
| | 189,451 |
| | 162,128 |
| 0.4 cells | 28,585 |
| | 23,253 |
| | 824,742 |
| | 64,945 |
| 0 cells | 1,432 |
| | 1,202 |
| | 1,258 |

Example 8

To demonstrate the reactivity and specificity of the probes directed to *N. meningitidis* 16S rRNA, a mixture of probes containing acridinium ester labeled oligonucleotides synthesized with the sequence 5'-CGCTGATATTAGCAACAGCC-3' (SEQ ID NO. 15) or sequence 5'-CGCTGGTATTAGCAACAGCC-3', (SEQ ID NO. 16), and unlabeled helper probes synthesized with the sequence 5'-TTTTCTTCCCTGACAAAAGTCCTTTACAACCCGAAGGC-3' (SEQ ID NO. 17 and 5'-GCCGGTGCTTATTCTTCAGGTACCGTCATCAG-3' (SEQ ID NO. 18), were hybridized to nucleic acid in lysates prepared from fresh cultures of the Neisseria species listed below. Each lysate was tested with a probe directed to a conserved region of 23S rRNA to confirm the lysis of the organism and integrity of the rRNA.

TABLE 8

Reactivity and specificity of probes directed to *N. meningitidis* 16S rRNA.

| Organism | ATCC No. | RLU with probe mix* | RLU with conserved probe |
|---|---|---|---|
| *N. cinerea* | 14685 | 736,927 | 59,831 |
| *N. denitrificans* | 14686 | 581 | 50,391 |
| *N. elongata* | 25295 | 1,511 | 52,017 |
| *N. elongata* subspecies *glycolytica* | 29315 | 618 | 53,312 |
| *N. flavescens* | 13120 | 1,316 | 53,397 |
| *N. gonorrhoeae* | 9793 | 1,826 | 62,658 |
| *N. gonorrhoeae* | 9827 | 753 | 60,252 |
| *N. gonorrhoeae* | 9830 | 4,832 | 58,346 |
| *N. gonorrhoeae* | 10150 | 1,139 | 61,573 |
| *N. gonorrhoeae* | 10874 | 759 | 58,291 |
| *N. gonorrhoeae* | 11689 | 4,824 | 60,039 |
| *N. gonorrhoeae* | 19088 | 910 | 53,594 |
| *N. gonorrhoeae* | 19424 | 851 | 60,372 |
| *N. gonorrhoeae* | 21824 | 746 | 62,153 |
| *N. gonorrhoeae* | 27630 | 1,829 | 53,241 |
| *N. gonorrhoeae* | 33084 | 784 | 62,696 |
| *N. gonorrhoeae* | 35541 | 431 | 59,229 |
| *N. lactamica* | 23970 | 3,497 | 54,255 |
| *N. meningitidis* serogroup A | 13077 | 844,739 | 54,292 |
| *N. meningitidis* serogroup B | 23255 | 722,108 | 61,439 |

TABLE 8-continued

Reactivity and specificity of probes directed to *N. meningitidis* 16S rRNA.

| Organism | ATCC No. | RLU with probe mix* | RLU with conserved probe |
|---|---|---|---|
| *N. meningitidis* serogroup B | 13090 | 704,890 | 57,321 |
| *N. meningitidis* serogroup B | 23251 | 761,475 | 58,545 |
| *N. meningitidis* serogroup C | 13103 | 770,221 | 63,704 |
| *N. meningitidis* serogropu C | 13106 | 761,099 | 60,928 |
| *N. meningitidis* serogropu C | 13102 | 752,743 | 62,351 |
| *N. meningitidis* serogroup C | 13111 | 711,196 | 59,635 |
| *N. meningitidis* serogroup C | 13109 | 768,874 | 63,295 |
| *N. meningitidis* serogroup C | 13110 | 676,060 | 58,150 |
| *N. meningitidis* serogroup C | 13112 | 543,492 | 54,921 |
| *N. meningitidis* serogroup C | 23248 | 321,600 | 59,308 |
| *N. meningitidis* serogroup D | 13113 | 770,893 | 56,429 |
| *N. meningitidis* group E | 35558 | 797,072 | 58,882 |
| *N. meningitidis* serogroup L | 43828 | 559,406 | 61,534 |
| *N. meningitidis* serogroup W-135 | 43744 | 705,798 | 62,152 |
| *N. meningitidis* serogroup Y | 35561 | 778,600 | 54,938 |
| *N. meningitidis* serogroup Z | 35562 | 749,756 | 61,793 |
| *N. meningitidis* | 13095 | 726,612 | 52,614 |
| *N. meningitidis* | 13101 | 775,912 | 59,839 |
| *N. meningitidis* | 13804 | 785,737 | 61,790 |
| *N. meningitidis* | 43743 | 734,400 | 61,357 |
| *N. mucosa* | 19696 | 1,560 | 53,427 |
| *N. mucosa* subspecies *heidelbergensis* | 25999 | 1,761 | 59,306 |
| *N. sicca* | 29193 | 1,205 | 58,260 |
| *N. sicca* | 9913 | 2,203 | 57,764 |
| *N. subflava* | 14799 | 2,046 | 50,832 |
| Negative sample | | 5,251 | 124 |
| | | 467 | 132 |
| | | 1,691 | 138 |

*probe mix contained acridinium ester labeled probes synthesized with sequences of SEQ ID NO. 15 and SEQ ID NO. 16 and unlabeled helper probes synthesized with sequences of SEQ ID NO. 17 and SEQ ID NO. 18.

The data show that the mixture of probes allowed detection of all of the *N. meningitidis* strains tested. The probe mix did show a cross reaction with *N. cinerea,* an organism unlikely to be found in the same clinical samples as *N. meningitidis.* Treatment of patients with *N. cinerea* infections would be the same as for patients infected with *N. meningitidis.*

Example 9

This example demonstrates the specificity of the amplification and detection assay. Thirty pmol of the promoter-primer comprising SEQ. ID. NO. 7 and 30 pmol of the primer comprising SEQ. ID. NO. 9 were used in the assay with eleven different Neisseria species. Cell lysates were prepared as described in Example 5 and amplified and analyzed by hybridization using the conditions described in Example 1. Twenty microliters of the amplification reactions were hybridized to an acridinium ester labeled probe synthesized with sequence 5'-GCCAATATCGGCGGCCGATG-3' (SEQ ID NO. 3) and an unlabeled helper probe synthesized with the sequence 5'-ACGGTACCTGAAGAATAAGCACCGGCTAACTACGTG-3' (SEQ ID NO. 4), or an acridinium ester labeled probe synthesized with the sequence 5'-GGCTGTTGCTAATATCAGCG-3' (SEQ ID NO. 11) in the presence of unlabeled helper probes synthesized with sequences comprising SEQ ID NOs. 13 and 14, or an acridinium ester labeled probe synthesized with the sequence 5'-GGCTGTTGCTAATACCAGCG-3' (SEQ ID NO. 12) in the presence of unlabeled helper probes of SEQ ID NOs. 13 and 14.

TABLE 9

Specificity of an assay using amplification with oligonucleotides comprising SEQ ID NOs. 7 and 9 followed by detection with probes comprising SEQ ID NOs. 3, 11 or 12.

| | | | RLU | | |
|---|---|---|---|---|---|
| SEQ ID NOs.: | Probe | Probe to conserved regions of bacterial rRNA | 11 | 12 | 3 |
| Organism | Helpers ATCC No. | | 13 + 14 | 13 + 14 | 4 |
| *Neisseria cinerea* | 14685 | 2,468,721 | 540,699 | 1,804 | 1,633 |
| | | | 609,648 | 2,484 | 1,536 |
| | | | 575,050 | 1,943 | 1,494 |
| *Neisseria denitrificans* | 14686 | 2,339,034 | 740 | 644 | 1,563 |
| | | | 659 | 578 | 1,539 |
| *Neisseria elongata* | 25295 | 2,486,745 | 772 | 428 | 1,521 |
| | | | 738 | 3,297 | 1,528 |
| *Neisseria elongata* subspecies glycolytica | 29315 | 2,397,697 | 697 | 431 | 1,443 |
| | | | 954 | 813 | 1,528 |
| *Neisseria flavescens* | 13120 | 2,622,452 | 780 | 493 | 1,547 |
| | | | 874 | 481 | 1,610 |
| | | | 969 | 429 | 1,589 |
| *Neisseria lactamica* | 23970 | 2,299,619 | 736 | 410 | 1,621 |
| | | | 839 | 425 | 1,544 |
| | | | 1,583 | 428 | 1,559 |
| *Neisseria mucosa* | 19696 | 2,565,699 | 1,021 | 981 | 1,596 |
| | | | 1,408 | 559 | 6,781 |
| | | | 851 | 5,260 | 1,574 |
| *Neisseria mucosa heidelber-gensis* | 25999 | 2,927,147 | 653 | 367 | 1,430 |
| | | | 664 | 390 | 1,971 |
| *Neisseria sicca* | 9913 | 2,427,561 | 699 | 777 | 1,609 |
| | | | 847 | 477 | 1,552 |
| | | | 834 | 437 | 1,642 |
| *Neisseria sicca* | 29193 | 2,804,642 | 954 | 423 | 1,588 |
| | | | 615 | 388 | 1,505 |
| *Neisseria gonorrhoeae** | 19424 | N.T. | 3,826 | 419 | 586,358 |
| | | | 1,092 | 411 | 564,987 |
| | | | 2,390 | 388 | 554,134 |
| *Neisseria meningitidis** Serogroup A | 13077 | N.T. | 557,656 | 1,287 | 1,492 |
| | | | 621,180 | 1,009 | 1,509 |
| | | | 539,592 | 954 | 1,617 |

*purified RNA used at 500 pg per reaction.
N.T. = Not tested.

The data shown in the examples described above confirm that the novel amplification oligonucleotides herein described and claimed are capable of amplifying Neisseria nucleic acid and can be used in an assay to distinguish *Neisseria meningitidis* or *Neisseria gonorrhoeae* from each other, the closest known phylogenetic neighbours. None of the examples described herein are intended to limit the present invention to the embodiments of this disclosure, said invention being limited exclusively by the claims which follow.

What is claimed is:

1. A probe mix comprising:

a first hybridization assay probe comprising a first oligonuoleotide containing 10 to 100 nucleotide bases which hybridizes to at least 10 contiguous nucleotide bases of a first target nucleic acid region present in target nucleic acid from *Neisseria meningitidis* subtypes A, C, and L and which does not detectably hybridize to nucleic acid from *Neisseria gonorrhoeae* under stringent hybridization conditions, wherein said first oligonucleotide contains a region of at least 10 contiguous nucleotide bases which is at least 80% perfectly complementary to said at least 10 contiguous nucleotide bases of said first target region, said first target region being selected from the group consisting of:

SEQ ID NO. 11;

SEQ ID NO. 27;

SEQ ID NO. 15; and

SEQ ID NO. 25; and a second hybridization assay probe comprising a second oligonucleotide containing 10 to 100 nucleotide bases which hybridizes to at least 10 contiguous nucleotide bases of a second target nucleic acid region present in a target nucleic acid from *Neisseria meningitidis* subtype L and which does not detectably hybridize to nucleic acid from *Neisseria gonorrhoeae* under said hybridization conditions, wherein said second oligonucleotide contains a region of at least 10 contiguous nucleotide bases which is at least 80% perfectly complementary to said at least 10 contiguous nucleotide bases of said second target region, said second target region being selected from the group consisting of:

SEQ ID NO. 12;

SEQ ID NO. 26;

SEQ ID NO. 16; and

SEQ ID NO. 28.

2. The probe mix of claim 1 further comprising a helper oligonucleotide which hybridizes to a third target nucleic acid region present in target nucleic acid from *Neisseria meningitidis* under said hybridization conditions, thereby facilitating the hybridization of at least one of said probes to at least one of said first and second target regions.

3. The probe mix of claim 2, wherein said helper oligonucleotide contains 10 to100 nucleotide bases and hybridizes to at least 10 contiguous nucleotide bases of said third target region under said hybridization conditions, wherein said helper oligonucleotide contains a region of at least 10 contiguous nucleotide bases which is at least 80% perfectly complementary to said at least 10 contiguous nucleotide bases of said third target region, said third target region being selected from the group consisting of:

SEQ ID NO. 13;

SEQ ID NO. 35;

SEQ ID NO. 17;

SEQ ID NO. 37;

SEQ ID NO. 14;

SEQ ID NO. 36;

SEQ ID NO. 18; and

SEQ ID NO. 38.

4. The probe mix of claim 3 further comprising an amplification oligonucleotide, which, when contacted with a nucleic acid polymerase under amplification conditions, will bind to or cause extension through a nucleic acid region having a nucleotide base sequence selected from the group consisting of:

SEQ ID NO. 7;

SEQ ID NO. 43;

SEQ ID NO. 19;

SEQ ID NO. 49;

SEQ ID NO. 9;

SEQ ID NO. 45;

SEQ ID NO. 20;

SEQ ID NO. 51;

SEQ ID NO. 11;

SEQ ID NO. 27;

SEQ ID NO. 15;

SEQ ID NO. 25;

SEQ ID NO. 12;

SEQ ID NO. 26;

SEQ ID NO. 16; and

SEQ ID NO. 28.

5. The probe mix of claim 1 further comprising an amplification oligonucleotide, which, when contacted wit a nucleic acid polymerase under amplification conditions, will bind to or cause extension through a nucleic acid region having a nucleotide base sequence selected from the group consisting of:

SEQ ID NO. 7;
SEQ ID NO. 43;
SBQ ID NO. 19;
SEQ ID NO. 49;
SEQ ID NO. 9;
SEQ ID NO. 45;
SEQ ID NO. 20;
SEQ ID NO. 51;
SEQ ID NO. 11;
SEQ ID NO. 27;
SEQ ID NO. 15;
SEQ ID NO. 25;
SEQ ID NO. 12;
SEQ ID NO. 26;
SEQ ID NO, 16; and
SEQ ID NO. 28.

6. A kit for identifying the presence of *Neisseria meningitidis* in a sample, said kit comprising:

a first hybridization assay probe comprising a first oligonucleotide containing 10 to 100 nucleotide bases which hybridizes to at least 10 contiguous nucleotide bases of a first target nucleic acid region present in target nucleic acid from *Neisseria meningitidis* subtypes A, C, and L and which does not detectably hybridize to nucleic acid from *Neisseria gonorrhoeae* under stringent hybridization conditions, wherein said first oligonucleotide contains a region of at least 10 contiguous nucleotide bases which is at least 80% perfectly complementary to said at least 10 contiguous nucleotide bases of said first target region, said first target region being selected from the group consisting of:

SEQ ID NO. 11;
SEQ ID NO. 27;
SEQ ID NO. 15; and
SEQ ID NO. 25; and a second hybridization assay probe comprising a second oligonucleotide containing 10 to 100 nucleotide bases which hybridizes to at least 10 contiguous nucleotide bases of a second target nucleic acid region present in a target nucleic acid from *Neisseria meningitidis* subtype L and which does not detectably hybridize to nucleic acid from *Neisseria gonorrhoeae* under said hybridization conditions, wherein said second oligonucleotide contains a region of at least 10 contiguous nucleotide bases which is at least 80% perfectly complementary to said at least 10 contiguous nucleotide bases of said second target region, said second target region being selected from the group consisting of:

SEQ ID NO. 12;
SEQ ID NO. 26;
SEQ ID NO. 16; and
SEQ ID NO. 28.

7. The kit of claim 6 further comprising a helper oligonucleotide which hybridizes to a third target nucleic acid region present in target nucleic acid from *Neisseria meningitidis* under said hybridization conditions, thereby facilitating the hybridization of at least one of said probes to at least one of said first and second target regions.

8. The kit of claim 7, wherein said helper oligonucleotide contains 10 to 100 nucleotide bases and hybridizes to at least 10 contiguous nucleotide bases of said third target region under said hybridization conditions, wherein said helper oligonucleotide contains a region of at least 10 contiguous nucleotide bases which is at least 80% perfectly complementary to said at least 10 contiguous nucleotide bases of said third target region, said third target region being selected from the group consisting of:

SEQ ID NO. 13;
SEQ ID NO. 35;
SEQ ID NO. 17;
SEQ ID NO. 37;
SEQ ID NO. 14;
SEQ ID NO. 36;
SEQ ID NO. 18; and
SEQ ID NO. 38.

9. The kit of claim 6 further comprising:

a first helper oligonucleotide containing 10 to 100 nucleotide bases which hybridizes to at least 10 contiguous nucleotide bases of a third target nucleic acid region present in target nucleic acid from *Neisseria meningitidis* under said hybridization conditions, wherein said first helper oligonucleotide contains a region of at least 10 contiguous nucleotide bases which is at least 80% perfectly complementary to said at least 10 contiguous nucleotide bases of said third target region, said third target region being selected from the group consisting of:

SEQ ID NO. 13;
SEQ ID NO. 35;
SEQ ID NO. 17; and
SEQ ID NO. 37; and a second helper oligonucleotide containing 10 to 100 nucleotide bases which hybridizes to at least 10 contiguous nucleotide bases of a fourth target nucleic acid region present in target nucleic acid from *Neisseria meningitis* under said hybridization conditions, wherein said second helper oligonucleotide contains a region of at least 10 contiguous nucleotide bases which is at least 80% perfectly complementary to said at least 10 contiguous nucleotide bases of said fourth target region, said fourth target region being selected from the group consisting of:

SEQ ID NO. 14;
SEQ ID NO. 36;
SEQ ID NO. 18; and
SEQ ID NO. 38.

10. The kit of claim 8 further comprising an amplification oligonucleotide, which, when contacted with a nucleic acid polymerase under amplification conditions, will bind to or cause extension through a nucleic acid region having a nucleotide base sequence selected from the group consisting of:

SEQ ID NO. 7;
SEQ ID NO. 43;
SEQ ID NO. 19;
SEQ ID NO. 49;
SEQ ED NO. 9;
SEQ ID NO. 45;
SEQ ID NO. 20;
SEQ ID NO. 51;
SEQ ID NO. 11;
SEQ ID NO, 27;

SEQ ID NO. 15;

SEQ ID NO. 25;

SEQ ID NO. 12;

SEQ ID NO. 26;

SEQ ID NO. 16; and

SEQ ID NO.28.

11. The kit of claim 6 further comprising an amplification oligonucleotide, which, when contacted with a nucleic acid polymerase under amplification conditions, will bind to or cause extension through a nucleic acid region having a nucleotide base sequence selected from the group consisting of:

SEQ ID NO. 7;

SEQ ID NO. 43;

SEQ ID NO. 19;

SEQ ID NO. 49;

SEQ ID NO. 9;

SEQ ID NO. 45;

SEQ ID NO. 20;

SEQ ID NO. 51;

SEQ ID NO. 11;

SEQ ID NO. 27;

SEQ ID NO. 15;

SEQ ID NO. 25;

SEQ ID NO. 12;

SEQ ID NO. 26;

SEQ ID NO. 16; and

SEQ ID NO. 28.

12. A method for detecting the presence of *Neisseria meningitidis* in a sample, said method comprising:

contacting said sample under stringent hybridization conditions with first and second hybridization assay probes, wherein:

said first hybridization assay probe comprises a first oligonucleotide containing 10 to 100 nucleotide bases which hybridizes to at least 10 contiguous nucleotide bases of a first target nucleic acid region present in target nucleic acid from *Neisseria meningitidis* subtypes A, C, and L and which does not detectably hybridize to nucleic acid from *Neisseria gonorrhoeae* under stringent hybridization conditions, wherein said first oligonucleotide contains a region of at least 10 contiguous nucleotide bases which is at least 80% perfectly complementary to said at least 10 contiguous nucleotide bases of said first target region, said first target region being selected from the group consisting of:

SEQ ID NO. 11;

SEQ ID NO. 27;

SEQ ID NO. 15; and

SEQ ID NO. 25; and said second hybridization assay probe comprises a second oligonucteotide containing 10 to 100 nucleotide bases which hybridizes to at least 10 contiguous nucleotide bases of a second target nucleic acid region present in a target nucleic acid from *Neisseria meningitidis* subtype L and which does not detectably hybridize to nucleic acid from *Neisseria gonorrhoeae* under said hybridization conditions, wherein said second oligonucleotide contains a region of at least 10 contiguous nucleotide bases which is at least 80% perfectly complementary to said at least 10 contiguous nucleotide bases of said second target region, said second target region being selected from the group consisting of:

SEQ ID NO. 12;

SEQ ID NO. 26;

SEQ ID NO. 16; and

SEQ ID NO. 28; and detecting at least one of said probes hybridized to at least one of said first and second target regions as an indication of the presence of *Neisseria meningitidis* in said sample.

13. The method of claim 12 further comprising contacting said sample with a helper oligonucleotide which to hybridizes to a third target nucleic acid region present in target nucleic acid from *Neisseria meningitidis* under said hybridization conditions, thereby facilitating hybridization of at least one of said probes to at least one of said first and second target regions.

14. The method of claim 13, wherein said helper oligonucleotide contains 10 to 100 nucleotide bases and hybridizes to at least 10 contiguous nucleotide bases of said third target region under said hybridization conditions, wherein said helper oligonucleotide contains a region of at least 10 contiguous nucleotide bases which is at least 80% perfectly complementary to said at least 10 contiguous nucleotide bases of said third target region, said third target region being selected from the group consisting of:

SEQ ID NO. 13;

SEQ ID NO. 35;

SEQ ID NO. 17;

SEQ ID NO. 37;

SEQ ID NO 14;

SEQ ID NO. 36;

SEQ ID NO. 18; and

SEQ ID NO. 38.

15. The method of claim 14 further comprising:

contacting said sample under amplification conditions with an amplification oligonucleotide, which, when contacted with a nucleic acid polymerase under said amplification conditions, will bind to or cause extension through a nucleic acid region having a nucleotide base sequence selected from the group consisting of:

SEQ ID NO. 7;

SEQ ID NO. 43;

SEQ ID NO. 19;

SEQ ID NO. 49;

SEQ ID NO. 9;

SEQ ID NO. 45;

SEQ ID NO. 20;

SEQ ID NO. 51;

SEQ ID NO. 11;

SEQ ID NO. 27:

SEQ ID NO. 15;

SEQ ID NO. 25;

SEQ ID NO. 12;

SEQ ID NO. 26;

SEQ ID NO. 16; and

SEQ ID NO. 28; and incubating said sample under said amplification conditions, wherein said amplification oligonucleotide optionally has a nucleic acid sequence recognized by an RNA polymerase or which enhances initiation or elongation by an RNA polymerase.

16. The method of claim 12 further comprising:

contacting said sample under amplification conditions with an amplification oligonucleotide, which, when contacted with a nucleic acid polymerase under said amplification conditions, will bind to or cause extension through a nucleic acid region having a nucleotide base sequence selected from the group consisting of:

SEQ ID NO. 7;
SEQ ID NO. 43;
SEQ ID NO. 19;
SEQ ID NO. 49;
SEQ ID NO. 9;
SEQ ID NO. 45;
SEQ ID NO. 20;
SEQ ID NO. 51;
SEQ ID NO. 11;
SEQ ID NO. 27;
SEQ ID NO. 15;
SEQ ID NO. 25;
SEQ ID NO. 12;
SEQ ID NO. 26;
SEQ ID NO. 16; and
SEQ ID NO. 28; and incubating said sample under said amplification conditions, wherein said amplification oligonucleotide optionally has a nucleic acid sequence recognized by an RNA polymerase or which enhances initiation or elongation by an RNA polymerase.

17. The method of claim 16 further comprising contacting said sample with a helper oligonucleotide which hybridizes to a third target nucleic acid region present in target nucleic acid from *Neisseria meningitidis* under said hybridization conditions, thereby facilitating hybridization of at least one of said probes to at least one of said first and second target regions.

18. The method of claim 17, wherein said helper oligonucleotide contains 10 to 100 nucleotide bases and hybridizes to at least 10 contiguous nucleotide bases of said third target region under said hybridization conditions, wherein said helper oligonucleotide contains a region of at least 10 contiguous nucleotide bases which is at least 80% perfectly complementary to said at least 10 contiguous nucleotide bases of said third target region, said third target region being selected from the group consisting of:

SEQ ID NO 13;
SEQ ID NO. 35;
SEQ ID NO. 17;
SEQ ID NO. 37;
SEQ ID NO. 14;
SEQ ID NO. 36;
SEQ ID NO. 18; and
SEQ ID NO 38.

* * * * *

SEQUENCE LISTING (1) GENERAL INFORMATION:

(iii) NUMBER OF SEQUENCES: 56

(2) INFORMATION FOR SEQ ID NO: 1:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 1:

GAACGTACCG GGTAGCGG 18

(2) INFORMATION FOR SEQ ID NO: 2:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 2:

GGGATAACTG ATCGAAAGAT CAGCTAATAC CGCATACG 38

(2) INFORMATION FOR SEQ ID NO: 3:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 3:

GCCAATATCG GCGGCCGATG 20

(2) INFORMATION FOR SEQ ID NO: 4:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 4:

ACGGTACCTG AAGAATAAGC ACCGGCTAAC TACGTG 36

(2) INFORMATION FOR SEQ ID NO: 5:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 5:

GTCCCCTGCT TTCCCTCTCA AGAC 24

(2) INFORMATION FOR SEQ ID NO: 6:

(i) SEQUENCE CHARACTERISTICS:
(A) LENGTH: 28 base pairs
(B) TYPE: nucleic acid
(C) STRANDEDNESS: single -continued (D) TOPOLOGY: linear (xi) SEQUENCE DESCRIPTION: SEQ ID NO: 6:

GGCGAGTGGC GAACGGGTGA GTAACATA 28

(2) INFORMATION FOR SEQ ID NO: 7:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 7:

GCTGCTGCAC GTAGTTAGCC GGTGCTTATT CTTCAG 36

(2) INFORMATION FOR SEQ ID NO: 8:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO: 8:

GTTAGCCGGT GCTTATTCTT CAGGTACCGT CATCG 35

(2) INFORMATION FOR SEQ ID NO: 9:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO: 9:

CGGGTTGTAA AGGACTTTTG TCAGGGAAGA AAAGGCCGTT 40

(2) INFORMATION FOR SEQ ID NO: 10:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 10:

GAAGGCCTTC GGGTTGTAAA GGAC 24

(2) INFORMATION FOR SEQ ID NO: 11:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 11:

GGCTGTTGCT AATATCAGCG 20

(2) INFORMATION FOR SEQ ID NO: 12:

(i) SEQUENCE CHARACTERISTICS:
(A) LENGTH: 20 base pairs
(B) TYPE: nucleic acid
(C) STRANDEDNESS: single
(D) TOPOLOGY: linear -continued (xi) SEQUENCE DESCRIPTION: SEQ ID NO: 12:

GGCTGTTGCT AATACCAGCG 20

(2) INFORMATION FOR SEQ ID NO: 13:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 13:

GCCTTCGGGT TGTAAAGGAC TTTTGTCAGG GAAGAAAA 38

(2) INFORMATION FOR SEQ ID NO: 14:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO: 14:

GCTGATGACG GTACCTGAAG AATAAGCACC GGC 33

(2) INFORMATION FOR SEQ ID NO: 15:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 15:

CGCTGATATT AGCAACAGCC 20

(2) INFORMATION FOR SEQ ID NO: 16:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 16:

CGCTGGTATT AGCAACAGCC 20

(2) INFORMATION FOR SEQ ID NO: 17:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 17:

TTTTCTTCCC TGACAAAAGT CCTTTACAAC CCGAAGGC 38

(2) INFORMATION FOR SEQ ID NO: 18:

(i) SEQUENCE CHARACTERISTICS:
(A) LENGTH: 33 base pairs
(B) TYPE: nucleic acid
(C) STRANDEDNESS: single
(D) TOPOLOGY: linear -continued (xi) SEQUENCE DESCRIPTION: SEQ ID NO: 18:

GCCGGTGCTT ATTCTTCAGG TACCGTCATC AGC 33

(2) INFORMATION FOR SEQ ID NO: 19:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 19:

CTGAAGAATA AGCACCGGCT AACTACGTGC AGCAGC 36

(2) INFORMATION FOR SEQ ID NO: 20:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO: 20:

AACGGCCTTT TCTTCCCTGA CAAAAGTCCT TTACAACCCG 40

(2) INFORMATION FOR SEQ ID NO: 21:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO: 21:

CGATGACGGT ACCTGAAGAA TAAGCACCGG CTAAC 35

(2) INFORMATION FOR SEQ ID NO: 22:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 22:

GTCCTTTACA ACCCGAAGGC CTTC 24

(2) INFORMATION FOR SEQ ID NO: 23:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 23:

GTCTTGAGAG GGAAAGCAGG GGAC 24

(2) INFORMATION FOR SEQ ID NO: 24:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO: 24:

-continued

TATGTTACTC ACCCGTTCGC CACTCGCC 28

(2) INFORMATION FOR SEQ ID NO: 25:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 25:

GGCUGUUGCU AAUAUCAGCG 20

(2) INFORMATION FOR SEQ ID NO: 26:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 26:

GGCUGUUGCU AAUACCAGCG 20

(2) INFORMATION FOR SEQ ID NO: 27:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 27:

CGCUGAUAUU AGCAACAGCC 20

(2) INFORMATION FOR SEQ ID NO: 28:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 28:

CGCUGGUAUU AGCAACAGCC 20

(2) INFORMATION FOR SEQ ID NO: 29:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 29:

CCGCTACCCG GTACGTTC 18

(2) INFORMATION FOR SEQ ID NO: 30:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 30:

-continued

CATCGGCCGC CGATATTGGC 20

(2) INFORMATION FOR SEQ ID NO: 31:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 31:

GAACGUACCG GGUAGCGG 18

(2) INFORMATION FOR SEQ ID NO: 32:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 32:

GCCAAUAUCG GCGGCCGAUG 20

(2) INFORMATION FOR SEQ ID NO: 33:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 33:

CCGCUACCCG GUACGUUC 18

(2) INFORMATION FOR SEQ ID NO: 34:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 34:

CAUCGGCCGC CGAUAUUGGC 20

(2) INFORMATION FOR SEQ ID NO: 35:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 35:

GCCUUCGGGU UGUAAAGGAC UUUUGUCAGG GAAGAAAA 38

(2) INFORMATION FOR SEQ ID NO: 36:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO: 36:

GCUGAUGACG GUACCUGAAG AAUAAGCACC GGC 33

-continued (2) INFORMATION FOR SEQ ID NO: 37:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 37:

UUUUCUUCCC UGACAAAAGU CCUUUACAAC CCGAAGGC 38

(2) INFORMATION FOR SEQ ID NO: 38:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO: 38:

GCCGGUGCUU AUUCUUCAGG UACCGUCAUC AGC 33

(2) INFORMATION FOR SEQ ID NO: 39:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO: 39:

GGGAUAACUG AUCGAAAGAU CAGCUAAUAC CGCAUACG 38

(2) INFORMATION FOR SEQ ID NO: 40:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 40:

ACGGUACCUG AAGAAUAAGC ACCGGCUAAC UACGUG 36

(2) INFORMATION FOR SEQ ID NO: 41:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 41:

GUCCCCUGCU UUCCCUCUCA AGAC 24

(2) INFORMATION FOR SEQ ID NO: 42:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO: 42:

GGCGAGUGGC GAACGGGUGA GUAACAUA 28

-continued (2) INFORMATION FOR SEQ ID NO: 43:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 43:

GCUGCUGCAC GUAGUUAGCC GGUGCUUAUU CUUCAG 36

(2) INFORMATION FOR SEQ ID NO: 44:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO: 44:

GUUAGCCGGU GCUUAUUCUU CAGGUACCGU CAUCG 35

(2) INFORMATION FOR SEQ ID NO: 45:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO: 45:

CGGGUUGUAA AGGACUUUUG UCAGGGAAGA AAAGGCCGUU 40

(2) INFORMATION FOR SEQ ID NO: 46:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 46:

GAAGGCCUUC GGGUUGUAAA GGAC 24

(2) INFORMATION FOR SEQ ID NO: 47:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 47:

GUCUUGAGAG GGAAAGCAGG GGAC 24

(2) INFORMATION FOR SEQ ID NO: 48:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO: 48:

UAUGUUACUC ACCCGUUCGC CACUCGCC 28

-continued (2) INFORMATION FOR SEQ ID NO: 49:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 49:

CUGAAGAAUA AGCACCGGCU AACUACGUGC AGCAGC 36

(2) INFORMATION FOR SEQ ID NO: 50:

(i) SEQUENCE CHARACTERISTICS:
(A) LENGTH: 35 base pairs
(B) TYPE: nucleic acid
(C) STRANDEDNESS: single
(D) TOPOLOGY: linear (xi) SEQUENCE DESCRIPTION: SEQ ID NO: 50:

CGAUGACGGU ACCUGAAGAA UAAGCACCGG CUAAC 35

(2) INFORMATION FOR SEQ ID NO: 51:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO: 51:

AACGGCCUUU UCUUCCCUGA CAAAAGUCCU UUACAACCCG 40

(2) INFORMATION FOR SEQ ID NO: 52:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO: 52:

GUCCUUUACA ACCCGAAGGC CUUC 24

(2) INFORMATION FOR SEQ ID NO: 53:

(i) SEQUENCE CHARACTERISTICS:
(A) LENGTH: 27 base pairs
(B) TYPE: nucleic acid
(C) STRANDEDNESS: single
(D) TOPOLOGY: linear (xi) SEQUENCE DESCRIPTION: SEQ ID NO: 53:

AATTTAATAC GACTCACTAT AGGGAGA 27

(2) INFORMATION FOR SEQ ID NO: 54:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 54:

GAGUAAAGUU AAUACCUUUG 20

(2) INFORMATION FOR SEQ ID NO: 55:

-continued

```
    (i) SEQUENCE CHARACTERISTICS:
         (A) LENGTH:          20 base pairs
         (B) TYPE:            nucleic acid
         (C) STRANDEDNESS:    single
         (D) TOPOLOGY:        linear

   (xi) SEQUENCE DESCRIPTION:   SEQ ID NO:  55:

GGCUGUUGCU AAUAUCAGCG                                          20


(2) INFORMATION FOR SEQ ID NO:  56:

    (i) SEQUENCE CHARACTERISTICS:
         (A) LENGTH:          20 base pairs
         (B) TYPE:            nucleic acid
         (C) STRANDEDNESS:    single
         (D) TOPOLOGY:        linear

   (xi) SEQUENCE DESCRIPTION:   SEQ ID NO:  56:

GGCUGUUGCC AAUAUCGGGG                                          20
```